US006814025B2

(12) United States Patent
Chen et al.

(10) Patent No.: US 6,814,025 B2
(45) Date of Patent: Nov. 9, 2004

(54) SYSTEM FOR OPTIMIZING THE PRODUCTION OF A MILK PRODUCING ANIMAL HERD

(75) Inventors: Fei Chen, Lynge (DK); Flemming Larsen, Haarby (DK); Henrik Hansen, Farum (DK); Thomas Mathiasen, København Ø (DK)

(73) Assignee: Lattec I/S, Hillerod (DK)

( * ) Notice: Subject to any disclaimer, the term of this patent is extended or adjusted under 35 U.S.C. 154(b) by 12 days.

(21) Appl. No.: 10/091,782

(22) Filed: Mar. 7, 2002

(65) Prior Publication Data

US 2002/0124803 A1 Sep. 12, 2002

Related U.S. Application Data

(60) Provisional application No. 60/334,585, filed on Dec. 3, 2001.

(30) Foreign Application Priority Data

Mar. 7, 2001 (EP) .......................................... 01610022
Dec. 3, 2001 (DK) ...................................... 2001 01790

(51) Int. Cl.[7] .............................. A01J 5/007; A01J 5/013
(52) U.S. Cl. ................................ 119/14.01; 119/14.14; 119/14.18
(58) Field of Search .......................... 119/14.01, 14.02, 119/14.08, 14.14, 14.15, 14.18

(56) References Cited

U.S. PATENT DOCUMENTS

| 3,841,756 A | 10/1974 | Grochowicz |
| 4,385,590 A | 5/1983 | Mortensen |
| 4,532,892 A | 8/1985 | Kuzara |

(List continued on next page.)

FOREIGN PATENT DOCUMENTS

| EP | 0518907 | 12/1992 |
| EP | 0638231 B1 | 2/1995 |
| EP | 0 657098 A1 | 6/1995 |
| EP | 0666475 | 8/1995 |

(List continued on next page.)

OTHER PUBLICATIONS

Translation of German patent publicaion DE 195 47 892 A1.
Notification of Transmittal of the International Search Report or the Declaration and International Search Report in PCT/DK 02/00148, dated Jun. 25, 2002.

(List continued on next page.)

Primary Examiner—Yvonne R. Abbott
(74) Attorney, Agent, or Firm—Hunton & Williams LLP

(57) ABSTRACT

A system for optimising the production performance of a milk producing animal herd is provided. The system comprises a milk sampling apparatus, an analytical apparatus comprising separate equipment for analyzing compounds or parameters that in the presence of compounds indicative of the physiological or nutritional condition of the herd member, generates detectable signals, and apparatus directing a part of the milk sample (directing apparatus) to each separate equipment, which is controlled by data for the physiological and nutritional state of a herd member, so that the directing apparatus is only activated at pre-selected points in time or at pre-selected time intervals in the production and/or lactation cycles. Specific compounds are compounds indicative of mastitis, including beta-N-acetylhexosaminidase (NAGase) E.C. 3.2.1.52 and lactate dehydrogenase (LDH), protein balance, including milk urea nitrogen (MUN) and total protein, ketosis, including acetolactate, beta-hydroxybutyrate, acetone and lipids, fat and state in reproduction cycle, including a steroid or peptide hormone, e.g., progesterone. Furthermore, the system comprises equipment for signal detection to record and process the signals, equipment to store data and equipment to produce data output. Methods for optimizing the production performance of a milk producing animal herd and an apparatus therefor.

117 Claims, 5 Drawing Sheets

U.S. PATENT DOCUMENTS

| | | | |
|---|---|---|---|
| 5,195,456 A * | 3/1993 | van der Lely et al. | 119/14.09 |
| 5,351,644 A | 10/1994 | Everett | |
| 5,568,788 A | 10/1996 | van den Berg et al. | |
| 5,704,311 A | 1/1998 | van den Berg | |
| 5,743,209 A | 4/1998 | Bazin et al. | |
| 5,873,323 A | 2/1999 | van den Berg et al. | |
| 6,115,679 A | 9/2000 | Rutter et al. | |
| 6,311,644 B1 * | 11/2001 | Pugh | 119/712 |
| 6,378,455 B1 | 4/2002 | Postma et al. | |
| 6,394,028 B1 * | 5/2002 | Birk | 119/14.08 |
| 6,405,672 B1 * | 6/2002 | De Mol et al. | 119/14.15 |

FOREIGN PATENT DOCUMENTS

| | | |
|---|---|---|
| EP | 0677243 B1 | 10/1995 |
| EP | 0764403 B1 | 3/1997 |
| EP | 0798959 B1 | 10/1997 |
| EP | 896222 | 2/1999 |
| EP | 1022937 B1 | 8/2000 |
| EP | 1123651 A3 | 8/2001 |
| EP | 1212936 A2 | 6/2002 |
| EP | 1212937 A1 | 6/2002 |
| EP | 1212938 A1 | 6/2002 |
| SE | 9902972 | 1/2001 |
| WO | 97/14297 | 4/1997 |
| WO | 98/20338 | 5/1998 |
| WO | WO 99/18774 | 4/1999 |
| WO | 99/51083 | 10/1999 |
| WO | 01/13709 A1 | 3/2001 |
| WO | 01/14887 A1 | 3/2001 |
| WO | 01/56369 A1 | 8/2001 |

OTHER PUBLICATIONS

Toby Mottram, "Automatic Monitoring of the health and metabolic status of dairy cows", Livestock Production Science, 1997, 48:209–217.

J. C. Mocquot, "Highlights of research and development work on an automatic milk analyser conducted in France" (Translation), pp. 308–317 (English Summary).

* cited by examiner

SYSTEM FOR OPTIMIZING THE PRODUCTION OF A MILK PRODUCING ANIMAL HERD

CROSS-REFERENCE TO RELATED APPLICATIONS

We claim priority from the following applications: EPO 01610022.4, filed Mar. 7, 2001; Denmark 2001 01790, filed Dec. 3, 2001: and U.S. application Ser. No. 60/334,585, filed Dec. 3, 2001. The entire contents of those applications are incorporated herein by reference.

FIELD OF THE INVENTION

The present invention relates generally to a system and methods for optimizing the production performance of a milk producing animal herd. More specifically, it provides automated or semi-automated means for dynamic real time analysis of milk compounds and parameters to provide quantitative analytical data that are indicative of the overall physiological and nutritional state of the milking animals and which, if required, permit appropriate corrective measures to be taken.

TECHNICAL BACKGROUND AND PRIOR ART

It is known to monitor the physiological and nutritional condition of milking animals, such as cows. It is also known to collect data from individual milking animals including data for milk yield and composition, health condition data, feeding scheme data and breeding data such as genetic data. A currently common procedure is to collect milk samples manually from individual milking animals at regular intervals and subsequently ship the samples to a central laboratory for chemical and biological analysis, thereby deriving information on the milk quality as well as the health condition of each individual milking animal.

In most milk producing countries, dairy herd improvement associations (DHIAs) will collect, evaluate and distribute such data relating to e.g. milk yield, milk quality and mastitis (i.e. Inflammation of the mammary gland). Based on these data that are available from the DHIAs, the dairy farmers can select the best milking animals for breeding, make appropriate adjustments to feeding schemes and control health to thereby optimize the milk production.

However, this current procedure for collecting such data is cumbersome and it requires a substantial amount of manpower as the milk samples are collected manually at the milk production unit and shipped to central laboratories to be analyzed. Consequently, milk from each milking animal is typically only analyzed 6–12 times per year. Using such a procedure it is not possible for the individual farm manager to take immediate corrective actions and, e.g., implement feeding scheme adjustments or initiate prophylactic measures or antibiotic treatments to control disease conditions.

This lack of access to updated information on significant production parameters involves several problems. As an example, the above procedure implies that milking cows may suffer from subclinical mastitis or other diseases for several weeks until detection hereof. An early detection of mastitis is highly desirable, as this condition has an important impact on the overall dairy farm business economy. A further important herd management parameter is that of selecting the optimal point in time for insemination of animals in heat. This is presently done by visual inspection of animals, which evidently is a cumbersome and unreliable procedure. Accordingly, it is economically important for dairy farmers to have instantaneous access to updated data that are indicative of heat and pregnancy in order to determine the optimal insemination time and control of pregnancy. Additionally, aberrant physiological conditions related to feeding such as ketosis, a metabolic disorder, and the overall metabolic balance of the milking animal, such as the protein balance in the rumen, are conditions for which there is a need to institute immediate corrective measures, which, however, is not possible unless up-to-date data that indicate the presence of such conditions are available.

Therefore, a substantial need exists for automated or semi-automated systems and methods that can provide the dairy farmer with instant access to real time data indicating the immediate physiological and nutritional condition of individual milking animals as the basis for taking instantaneous corrective actions to continuously improve the overall production performance of the milk producing herds including productivity of the milking animals, animal welfare and protection of the environment against pollution with animal waste, and with that the overall profitability of the dairy farm.

A review of research objectives for the development of monitoring and sensing systems for controlling the health of dairy cows has been given by Mottram (Livestock Production Science, 1997, 48:209–217).

Several automated systems for monitoring selected compounds and parameters in milk have been developed. Thus U.S. Pat. No. 5,873,323 discloses a method of milking animals automatically while determining whether the milking animal is diseased or in oestrus. Sensors are placed in the milking conduit system leading from the teat cups. The sensors measure simultaneously several parameters including milk flow, milk temperature and electric conductivity of the milk (mastitis detection). The data obtained by the measurements are provided to a computer which compares the new data with similar data from immediately preceding selected periods of time to identify aberrant values that indicate which animals are diseased or in oestrus.

U.S. Pat. No. 5,743,209 discloses a system and method for monitoring and controlling milk production at dairy farms that is capable of qualitative analysis of the composition of milk samples using IR/NIR optical probes. Compounds that are analyzed simultaneously include fat, protein, somatic cells (indicator for mastitis), casein, lactose and urea. EP 896 222 A3 discloses a system for monitoring and controlling protein utilization in animals by automatically analyzing the urea content in milk using a sensor unit containing urease. SE 9902972 discloses a method and a system for analyzing milk during the milking operation, including simultaneous analysis of somatic cells, "clots", salt ions and progesterone. The analyzing means are generally light emitter means and light detection means, however, there is, in very general terms, referred to the use of a biosensor for measuring, i.e., progesterone, urea and ketone bodies.

The achievement of the highest possible productivity of a milk producing animal herd is an extremely complicated task, as the productivity is highly dependent on a variety of factors including: (i) optimal utilization of feed rations which requires that feeding schemes are designed on an individual animal basis or a group basis and is continuously adjusted according to the milk yield (lactation state); (ii) tight control of subclinical and clinical disease conditions that have an adverse effect on milk yield and composition; (iii) optimal reproduction control including the selection of the most appropriate point in time for insemination to avoid any reduction of overall milk yield due to deferment of new pregnancy, and reliable detection of pregnancy.

Ideally, an automated or semi-automated system for optimizing the production performance of a milk producing animal herd should therefore have the capability to provide, on a real time basis, quantitative measurements of a combination of compounds and parameters in milk samples from individual herd members or a group of herd members that are indicative of all of (i) the health condition, (ii) the physiological condition, (iii) the nutritional and energy state, (iv) the state in the oestrus cycle and (v) pregnancy.

From the above, it is evident that the overall production characteristics of an individual herd member will vary considerably over times, e.g., depending on its state in the lactation cycle and the reproduction cycle which will, e.g., have a significant impact on the feed requirements and utilization of that particular herd member. This variation implies that the range of compounds and parameters that it is required to monitor at any given point in time varies.

In addition to being capable of generating data for all relevant milk compounds and parameters that are required to fully optimize the production performance of a milk producing animal herd, the ideal automated or semi-automated system should be cost-effective. This implies that the individual analytical processes should be based on relatively cheap methods. As it is described in the following, a significant reduction in costs can be achieved by designing the production performance monitoring system such that an individual milk sample collected at a given point in time is only analyzed for compounds or parameters that need to be analyzed at the particular point in time to optimize the production performance of the particular herd member or the particular group of herd members. Thus, to illustrate this point, compounds/parameters indicative of mastitis may be analyzed on a daily basis whereas compounds/parameters that are indicative of whether or not an animal is in heat need only be analyzed at pre-selected periods of time.

Additionally, it is highly advantageous that the ideal production performance monitoring system is capable of generating quantitative analytical data for selected compounds and parameters, for which even relatively small day-to-day variations are highly predictive for a change in the overall health condition, the physiological condition, nutritional and energy state, the state in the oestrus cycle or pregnancy of the individual herd member being tested. This requires that the system is provided with analytical means that permits frequent quantitative analysis to be made at a cost-effective level.

The present inventors have now developed a system for optimizing the production performance of a milk producing animal herd, which meets all of the above requirements of an ideal system for optimizing production performance of milk producing herds. The system is based on the findings that frequent and continuous real time measurements of one or more of a broad range of carefully selected compounds or parameters indicative of and related to the physiological and nutritional condition of individual milking animals provide the means of continuously optimizing the overall production performance of the milking animal herd and hence the profitability of the dairy farm.

In particular, it has been found that by combining parameters relating to mastitis, protein balance, energy balance and state in oestrus cycle in a system according to the invention it has become possible to substantially improve the productivity and the profitability of dairy farms, as the combination of such parameters has been found to provide detailed and reliable information resulting in a substantially better picture of the overall physiological and nutritional condition of milking animals, such as e.g. metabolic disorders and reproduction state.

SUMMARY OF THE INVENTION

It is therefore a primary objective of the invention to provide the means to optimize the productivity and profitability of a milk producing animal herd, in particular a herd of dairy cows. The objective is met by providing a novel automated or semi-automated system that is capable of real time analysis of a broad range of compounds and parameters in individual animal milk samples and to continuously process the thus obtained analytical data to provide, when required, the basis for taking immediate corrective steps to improve productivity of one or more herd members.

It is one significant feature of the system that the number of compounds or parameters out of those possible that is to be analyzed by the system at any given point in time is dependent, e.g., on the reproduction or lactation cycle state of the individual animal. This is made possible by operationally linking the analytical means to a database containing information on the reproduction and lactation state of each herd member or any other information that may be used to determine whether or not a particular milk compound or parameter should be analyzed at a particular point in time. In this manner the system operates in a "dynamic" mode.

Accordingly, the invention pertains in one aspect to an automated or semi-automated system for optimizing the production performance of a milk producing animal herd comprising a plurality of individual herd members each assigned a unique identification code that is recognizable by the system, the system comprising the following interconnected means:

(a) means for collecting a milk sample from an individual member of said herd, said means is connectable to the herd milking system, (b) means for recognizing the identification code of the individual herd member, (c) means for storing data including data for the physiological and nutritional state of said each individual herd member including data indicating point in time in the reproduction and lactation cycles, (d) means for analyzing plurality of compounds or parameters in a milk sample being collected, said means comprising:

(i) separate means for analyzing individual compounds or parameters in the milk sample, each of said separate means is capable of generating a detectable signal in the presence of an individual milk compound or parameter, (ii) means for directing a part of the milk sample to each separate analyzing means, said directing means being controlled by said means for storing data for the physiological and nutritional state of each individual herd member such that the directing means is only activated at pre-selected points in time or at pre-selected time intervals in the reproduction or lactation cycles, (iii) means for detecting signals generated in the presence of a compound or parameter being analyzed, (e) means for converting the detected signals to a set of data that is indicative of the physiological and/or nutritional condition of said individual herd member, (f) means for storage of said set of data indicative of the physiological and/or nutritional condition for said individual herd members, and (g) data output means.

In a further aspect there is provided a method for optimizing the production performance of a milk producing animal herd using the system as defined above. The method comprises the steps of:
(i) collecting at a milking site a milk sample from each individual member of the herd,
(ii) contacting said sample with the analyzing means that, in the presence of at least one compound or parameter indicative of the physiological and/or nutritional condition of the herd member, generates a detectable signal/detectable signals,
(iii) recording in the signal detection means the character of said signal(s) to provide a set of analytical data indicative of the presence and/or amount of said compound or parameter,
(iv) having the generated data processed to provide a set of data descriptive of the physiological and/or nutritional condition of the individual herd member, and
(v) taking, on the basis of the set of data provided, appropriate steps to improve or correct the physiological and/or nutritional condition of any of the herd members in need of such improvement or correction.

In yet a further aspect the invention relates to a method for optimizing the production performance of a milk producing animal herd comprising a plurality of individual herd members using an automated or semi-automated system for optimizing the production performance of a milk producing animal herd, the system comprising the following interconnected means:
(a) means for collecting a milk sample from an individual member of said herd, said means is connectable to the herd milking system,
(b) means for recognizing a unique identification code assigned to each of the individual herd member,
(c) means for storing data including data for the physiological and nutritional state of said each individual herd member including data indicating point in time in the reproduction and lactation cycles,
(d) means for analyzing a plurality of compounds or parameters in a milk sample being collected, said plurality of compounds or parameters at least including a compound or parameter indicative of mastitis, a compound indicative of the reproduction cycle state, at least one compound indicative of the protein balance of the herd member and at least one compound indicative of the energy balance state of the herd member, said analyzing means comprising
 (i) separate means for analyzing individual compounds or parameters in the milk sample, each of said separate means is capable of generating a detectable signal in the presence of an individual milk compound or parameter, and
 (ii) means for detecting signals generated in the presence of a compound or parameter being analyzed,
(e) means for converting the detected signals to a set of data that is indicative of the physiological and/or nutritional condition of said individual herd member,
(f) means for storage of said set of data descriptive of the physiological and/or nutritional condition for said individual herd members, and
(g) data output means, the method comprising the steps of:
 (i) collecting at a milking site a milk sample from each individual member of the herd,
 (ii) contacting said sample with the analyzing means that, in the presence of at least one compound or parameter indicative of the physiological and/or nutritional condition of the herd member, generates a detectable signal detectable signals,
 (iii) recording in the signal detection means the character of said signal(s) to provide a set of analytical data indicative of the presence and/or amount of said compound or parameter,
 (iv) having the generated data processed to provide a set of data descriptive of the physiological and/or nutritional condition of the individual herd member, and
 (v) taking, on the basis of the set of data provided, appropriate steps to improve or correct the physiological and/or nutritional condition of any of the herd members in need of such improvement or correction.

In a further aspect the invention provides an apparatus for analyzing a plurality of compounds or parameters in a milk sample of an individual member of a milk producing animal herd, said apparatus comprising:
(i) separate means for analyzing individual compounds or parameters in the milk sample, each of said separate means is capable of generating a detectable signal in the presence of an individual sample compound or parameter,
(ii) means for directing a part of the milk sample to each separate analyzing means, said directing means being controlled by means for storing data for the physiological and nutritional state at each individual herd member, including data indicating point in time in the reproduction and lactation cycles of said herd member, such that the directing means is only activated at pre-selected points in time or at pre-selected time intervals in the production or lactation cycles of the individual herd member.

DETAILED DISCLOSURE OF THE INVENTION

The primary objective of the invention is to provide an automated or semi-automated system for optimizing the production performance of a milk producing animal herd.

As used herein, the term "automated" implies that the system can be operated substantially without manual operations. Thus, the term indicates that milk samples are automatically collected on-line at the milking site from the milking system and automatically transported to analytical means which in turn automatically generate analytical data that are processed automatically to update the system and to provide instructions to the farm management for corrective measures. The milking site may be a milking site of an automatic milking system tar freely moving milking animal or one of several milking sites in a conventional milking system such as a herringbone milking system. The milking site may also be at rotating or parallel milking parlors.

The term "semi-automated" as used herein refers to a system where at least part of the operations of the system involves some manual operation, e.g. manual transport of samples to the analytical means.

The term "production performance" as used herein, is intended to mean the production performance in its broadest aspect. Thus, included in this term is milk production, including milk quantity and quality, reproductive performance of herd members, e.g., the number of offspring per milking animal and optimum utilization of feed rations. Although the system is particularly useful in dairy cow herds, the term "milk producing animal herd" is intended to mean any herd comprising milk producing animals including, e.g., sheep, goats, camels and buffaloes.

It is an advantageous feature of the present system that it is capable of recognizing unique identification codes carried by the herd members, such as, e.g., bar codes, e.g., involving an alpha-numeric code, or other electronic signal types generated by electronic devices such as radio transmitters, assigned to each individual member of the herd.

The system of the invention comprises several operationally interconnected elements which may or may not be physically connected. As one such element, the system of the invention comprises means for collecting at a milking site milk samples from individual members of a milking animal herd. Typically, the sample collecting means is the physical connection between the milking points and the analyzing means. The function of the sample collecting means is to collect milk samples to be analyzed at the appropriate time during the milking process and to subsequently transport and present the samples to the analyzing means. However, in both automated and semi-automated systems it is conceivable that the sample collecting means is not in direct physical connection with the analyzing means, but the system may be designed so as to deliver a sample being collected to a separate means for storing milk samples, which in turn can be operationally connected to the analyzing means as it will be explained in the following.

In useful embodiments, the sample collecting means is adapted to collect a milk sample from an individual mammary gland of a herd member or alternatively, to collect a sample combining milk from two or more mammary glands of the herd member including a sample where milk from all mammary glands is combined.

In a presently preferred embodiment, the sample collecting means is capable of collecting a proportional milk sample which is representative of the average composition of the total milk produced during the milking of each individual animal. Such a proportional sample can be collected by leading a proportion of an area of the milk flow to a sample storage container or by leading all the milk in a flow to a sample storage container for a pre-selected time interval of the milking operation, or by a combination of these principles. The former principle implies the advantage that it is not required to provide the sampling means with moving parts such as magnetic valves. The sample collecting means may comprise means for storing a milk sample being collected.

Suitable means for that purpose include a container, which is connected to the general milking system line, optionally by pressure control means permitting that the pressure in the container can be different from that of the milking system. With such a design the pressure in the container is the same as that of the milking system when the milk sample is being collected, but when a subsample of the total sample should be generated for analysis, the container is subjected to a pressure that exceeds the pressure of the milking system. The sample storage means can be positioned at any location which permits the subsequent and/or parallel transport of subsamples to the analyzing means to occur such as, e.g., at the milking site.

When a milk sample is stored in the storage means, a certain separation of milk components such as fat may occur. As it is critical that subsamples that are to be contacted with the analyzing means have the natural composition it may be appropriate to provide the means for storing a milk sample with means for continuously mixing, homogenizing or agitating the milk sample during storage. One example of such means is a magnetic stirring device.

It is generally required to design the sample storage means such that it can be flushed or cleaned in between samples. Suitable flushing or cleaning media include milk, air, water, detergent solutions or combinations thereof. During storage of a sample, it may be appropriate to add a buffer solution or a dilute solution to the sample. Additionally, it may be advantageous to provide the sample storage means with temperature control means. Accordingly, in useful embodiments, the sample collecting means further comprises or is operationally connected with at least one of (i) means permitting the sample collecting means to be cleaned between samples, (ii) means for storing a buffer solution or a dilute solution, (iii) means tar connecting the means for storing a milk sample to the analytical means, the means for storing a buffer solution or a dilute solution, the milking system and/or a sample discharge outlet, (iv) means for controlling the temperature of the milk sample being collected and (v) means for transporting the milk sample being collected. Additionally, the means for collecting a milk sample may comprise means for apportioning a milk subsample to the analyzing means. The general function of such means is to divide the total sample collected during the milking operation into one or more subsamples which is/are transported to the analyzing means and the remaining part of the sample which may be led to the milk bulk tank or discharged.

In one particular embodiment the sample collecting means comprises means for simultaneously storing a plurality of milk samples, i.e. milk samples from several individual animals. Such means may e.g. be in the form of a device having several separate compartments or containers for receiving individual samples. In one specific embodiment, such a device comprising a plurality of milk storage compartments or containers is a device that can be inserted into and engaged with the milk collecting means prior to collecting milk samples and is removable herefrom when the plurality of samples is collected for bringing it into operational contact with the analytical means.

The interfacing between sample collecting means and the milking system may be at any suitable points of the milking system. Thus, as suitable examples the interfacing elements may be connected to teat cups, teat tubes, milk metering devices, milk flow metering devices, milk containers and any milk transporting tubing elements. The nature of the interfacing will depend on the material at the site of connection as it will be readily appreciated by the skilled artisan. In one specific embodiment, the means for collecting a milk sample is connected to a tubing element of the milking system and is provided with a separate milk metering device. When the system of the invention is designed so as to permit sampling from individual mammary glands, the interfacing is preferably at individual teat cups or teat tubes.

A major objective of the invention is, as it is mentioned above, to provide a system that provides the means to optimize the production performance of a milk producing animal herd. A key element in the system is to provide for real time "dynamic" analysis of a range of compounds and parameters to generate analytical data that, when assessed separately or in combination and, optionally compared with previous data for the compounds or parameters, enable the herd manager to take appropriate corrective actions. The compounds and parameters to be analyzed are selected so as to provide for each herd member a comprehensive description of the health condition, physiological condition, energy and nutritional condition and state in reproduction cycle.

Accordingly, the system comprises in a preferred embodiment separate means for analyzing individual compounds or parameters in the milk sample that include means for analyzing at least one compound or parameter selected from the group consisting of a compound or parameter that is indicative of mastitis, a compound or parameter that is indicative of the reproduction cycle state of the milking animal and a compound or parameter that is indicative of the energy and nutritional state of the milking animal.

In the present context the term "mastitis" is to be understood as an inflammatory reaction of the mammary gland. Mastitis is the most loss-making production disease in the dairy industry. Thus, annual losses from mastitis in the USA amount to more than 2 billion dollars. Decreased milk production, discarded milk, reduced raw milk quality, medical costs and higher culling rates are the most important economic consequences of both subclinical and clinical mastitis. However, public health, product quality and shelf life, animal care, and consumer perception provide additional economic incentives to control mastitis. Mastitis is positively correlated to milk yield and despite much effort little improvement in reduction of incidence of mastitis, if any, has occurred during the last couple of decades. Thus, it is of major importance for the dairy farmer to have an early, or more preferably, an instant indication of mastitis, including subclinical mastitis, in order to minimize the production losses.

Mastitis is often characterized by the cause of the disease which may be infectious, traumatic or toxic. When mastitis occurs, the intramammary tissue is damaged, followed by an increased permeability between the blood and milk compartments, resulting in changes in milk composition. Subclinical mastitis can only be detected by laboratory tests whereas clinical mastitis can be detected by clinical examination of the milk and/or the udder. The pathogens most often found in connection with mastitis are bacteria such as e.g. *Escherichia coli, Staphylococcus aureus, Micrococcus spp., Streptococcus uberis, Streptococcus agalactiae* and *Streptococcus dysgalactiae*.

Several compounds that are not present in milk from healthy mammary glands and/or the amounts of which are elevated in mastitic milk are indicative of mastitis. Such compounds include somatic cells, enzymes, proteins, fat, lipids, minerals and trace elements. Accordingly, analysis of milk for any such compounds including as examples fatty acids, whey proteins, κ-casein, immunoglobulins, proteose peptones, serum albumin, lactoferrin, and mineral compounds such as sodium, chloride, iron and copper may be useful in the present invention. Enzymes may be particularly suitable as compounds indicative of mastitis. Representative examples of such enzymes include catalase, lactate dehydrogenase (LDH), alkaline phosphatase, acid phosphatase, carboxylesterase, arylesterase, β-glucuronidase, lactoperoxidase, lipase, lysozyme, xanthine oxidase, plasmin and beta-N-acetylhexosaminidase (NAGase).

Accordingly, in one useful embodiment the system of the invention comprises separate analyzing means for analyzing a compound or parameter indicative of mastitis that is selected from the group consisting of somatic cells, microbial cells or parts thereof, an enzyme, a protein, a fat, a lipid, a mineral, a trace element, milk temperature, conductivity of the milk, a particle that is separable by filtration and any combination thereof.

An example of a specific compound the amount of which is indicative of mastitis is beta-N-acetylhexosaminidase (NAGase), an intracellular, lysosomal enzyme (E.C. 3.2.1.52), belonging to a group of glycosidases. NAGase is involved in glycoprotein catabolism and is present in plasma. The concentration of NAGase in plasma is typically 11 to 20 times of that found in normal milk and two to four times that of mastitic milk. The function of NAGase in mammary secretions is presently not known. In one embodiment, the system of the invention comprises separate analyzing means for analyzing NAGase that is capable of detecting an amount of NAGase which is in the range of 0 to 0.1 U/ml including 0.01 to 0.09 such as 0.02 to 0.08, e.g., 0.03 to 0.05 U/ml.

In the present context, a further enzyme of interest as an indicator of mastitis is lactate dehydrogenase (LDH) that is also normally present in plasma at substantially higher levels than in milk and the amount of which is therefore increased in milk from inflamed mammary glands. In a further embodiment, the present system comprises separate analyzing means for analyzing LDH that is capable of detecting an amount of LDH in milk which is in the range 100 to 2000 U/ml such as the range of 200 to 1500 U/ml., e.g., the range of 500 to 1000 U/ml.

In order to optimize the overall production performance of a milk producing animal herd, it is pertinent to closely monitor the state in reproduction cycle of each individual animal in order to select the optimum time for insemination, i.e. to determine the optimum reception time in the cycle. However, it is difficult to visually observe and closely monitor, on an individual herd member basis, a large herd. It is particularly difficult to identify the first heat event after calving and lactation start in cows at the time interval between 40 and 65 days post calving. Therefore, automatic methods permitting reliable and frequent monitoring of the state in reproduction cycle are needed.

"State in reproduction cycle" is used herein to designate the different periods in the sexual cycle of female mammals during which they are in pro-oestrus, oestrus (in heat), di-oestrus and pregnancy, respectively. Compounds which, in accordance with the invention, may be applied to indicate reproduction cycle state may include hormones such as steroid or peptide hormones including as an example, the steroid hormone, progesterone that is produced by the corpus luteum in the ovaries and the placenta in all mammals.

Accordingly, in one preferred embodiment the system of the invention comprises separate analyzing means for analyzing a compound or parameter such as a hormone, the presence or amount of which in milk is indicative of the reproduction cycle state of the milking animal that is selected from the group consisting of a compound that indicates pro-oestrus, a compound that is indicative of oestrus (heat), a compound that indicates di-oestrus and a compound that indicates pregnancy. In this context, one presently preferred hormone is progesterone. In useful embodiments, the separate analyzing means for analyzing progesterone is capable of detecting an amount hereof in the milk sample which is in the range of 0 to 30 ng/ml, including 0 to 20 ng/ml, such as 1 to 15 ng/ml or 2 to 10 ng/ml.

The feeding of milking animals is a factor of the utmost importance in optimizing the production performance of the animals. A general problem in current dairy farming is that the individual milking animals are not continuously fed optimally. Thus, high yielding milking animals are as a matter of convenience frequently offered the same feed ration as low yielding milking animals. It is also a problem that the milk yield of the same individual herd member varies according to its state in the lactation cycle for which reason the nutrient requirements of the herd member are constantly changing. One important aspect in relation to the composition of the feed for milking animals is that the crude protein content of the feed should be continuously optimized in order to improve the overall crude protein balance of the milking animal. In the present context the term "protein balance" is used to designate the ratio between the amount of protein which is taken up by the milking animal and used for milk and tissue production, and the amount of urea excreted from the milking animal.

It is known to use the content of urea in milk as an indication of the protein balance of a milking animal, i.e. as an indicator of the milking animal's utilization of feed ration nitrogen. The urea concentration in the blood of milking animals vanes and is affected, e.g., by protein intake and urinary excretion. If the milking animal consumes feed with a content of crude protein that is too high for complete microbial conversion in the gastrointestinal tract, e.g., in the rumen of the milking animal, this will result in higher blood urea levels. As blood urea is freely diffiusible into milk, changes in blood urea levels will cause a corresponding change in milk urea level normally denoted milk urea nitrogen (MUN).

Accordingly, milk urea nitrogen (MUN) can be used in accordance with the invention as an indicator, e.g., for optimizing a feeding scheme and/or for pointing out possibilities for changing the composition of the feed. Thus, regular MUN measurements can be applied to precisely and instantaneously adjusting the nitrogen requirements of each individual milking animal. Additionally, MUN measurements can aid the dairy farmer in, e.g., reducing feed costs, to increase the overall milk protein yield, and to minimize nitrogen excretion into the environment.

In one useful embodiment the system of the invention therefore comprises separate analyzing means for analyzing a compound or parameter indicative of the energy and/or nutritional state of the milking animal which is a compound or parameter that is indicative of the protein balance of the milking animal including milk urea nitrogen (MUN) and total milk protein. It has been found that a combination of MUN and total milk protein values are particularly useful as an indication of protein balance. In useful embodiments, the system comprises separate analyzing means for analyzing a compound or parameter that is indicative of the protein balance of the milking animal which is capable of detecting an amount of MUN which is in the range of 0 to 1000 mg/l including 0 to 700 mg/l such as 10 to 500 mg/ml or 100 to 400 mg/ml.

As it is discussed above, the metabolic performance of the milking animal is particularly relevant for the overall production performance of each individual milking animal, and hence the entire herd. Ketosis is a metabolic disorder affecting the metabolic performance which is frequently encountered in dairy animals such as cows, in particular during certain periods of the lactation cycle. The primary cause of ketosis is a lack of available energy for the mammary gland in early lactation resulting in an aberrant energy balance of the animal. When milking animals are affected by this metabolic disorder, they typically lose weight and produce less milk. Immediate feed ration adjustment is needed to prevent and treat the disorder. The disorder is characterized by elevated levels of ketone bodies in the tissues and body fluids, including blood, milk and urine. In the present context "ketone bodies" includes compounds such as acetolactate, beta-hydroxybutyrate (BOHB) and acetone.

Accordingly, in one useful embodiment the system of the present invention comprises separate analyzing means for analyzing a compound or parameter that is indicative of the overall energy balance of the milking animal including a ketone body compound and the total milk fat content. In specific embodiments, the ketone body compound is selected from the group consisting of acetolactate, beta-hydroxybutyrate (BOHB) and acetone, in presently preferred embodiments, such analyzing means is capable of detecting an amount of BOHB in milk which is in the range of 0 to 0.7 mM including an amount hereof which is the range of 0.1 to 0.5 mM such as, e.g., in the range of 0.2 to 0.4 mM.

As it discussed above, it is one useful characteristic of the system of the invention that a range of compounds and parameters that, for each individual herd member provides a comprehensive picture of all of (i) the health condition, (ii) the physiological condition, (iii) the nutritional and energy state, (iv) the state in the oestrus cycle and (v) pregnancy can be analysed. Accordingly, in preferred embodiments the system of the invention comprises separate means for analyzing at least one compound or parameter selected from the group consisting of NAGase, lactate dehydrogenase (LDH), progesterone, milk urea nitrogen, total protein content, BOHB, total fat content and milk yield. In certain embodiments, the system comprises analyzing means for at least the following compounds/parameters: (i) an enzyme that is indicative of mastitis such as NAGase or LDH, a hormone compound indicative of state in the reproductive cycle such as progesterone, a compound indicative of protein balance such as MUN and/or total protein content and a compound indicative of the energy state such as acetone, a ketone body or BOHB.

In addition to these compounds and parameters, the system may comprise or may be linked to means for analyzing any other compound or parameter that may be present or occur in milk samples such as, e.g., somatic cells, filtrable clots/particles, pathogenic and saprophytic microorganisms including coliform bacteria, psychrotrophic bacteria or parts thereof such as fat, proteins, lipopolysaccharides, conductivity, added water, carbohydrates, immunogiobulins, enzymes such as, e.g., lactoperoxidase, lactoferrin, whey proteins, caseins, amino acids, fatty acids and residues of drugs including antibiotics.

As also discussed above, it is one advantageous feature of the invention that the parameters/compounds can be analyzed in a dynamic mode, i.e. that only those compounds or parameters which, at a given point in time of the reproduction and/or lactation cycle of the individual herd members should be analyzed in a particular milk sample. This is achieved by providing in the system means for storing data including data for the physiological and nutritional state of said each individual herd member including data indicating point in time in the reproduction and lactation cycles and by connecting such means operationally with means for analyzing a plurality of compounds or parameters in a milk sample being collected, comprising: (i) separate means for analyzing individual compounds or parameters in the milk sample, each of said separate means is capable of generating a detectable signal in the presence of an individual milk compound or parameter, (ii) means for directing a part or a subsample of the milk sample to each separate analyzing means, said directing means being controlled by the above means for storing data far the physiological and nutritional state of each individual herd member such that the directing means is only activated at pro-selected points in time or at pre-selected time intervals in the production or lactation cycles. In this connection, one interesting feature is that the means far storing data for the physiological and nutritional state of each individual herd member is continuously updated with new data, so that the selection of the range of compounds/parameters that are analyzed in a given sample at a given point in time is based on a constantly updated set of data for the particular herd member.

As illustrative examples, it may be appropriate to analyze about 20 samples for heat/pregnancy annually, e.g., 5 times per week in periods of expected oestrus and samples about 3 weeks post-oestrus and about 20 samples for detection of anoestrus. Analysis for compounds/parameters that are indicative of mastitis may be carried out at each milking or once every day. With respect to analysis for protein balance indicators, a suitable frequency may be once a week and may only be carried out for a proportion of the herd members, e.g., at least 10%, 20% or 30% of the herd members throughout the lactation period. Compounds that are indicators for the energy state of the animals such as BOHB, acetone or total fat content may, e.g., be analyzed once daily in the first two months of post-calving.

The analyzing means of the system may be selected from any analytical means known in the art for analyzing any of the above compounds/parameters. Illustrative examples of such analyzing means include enzyme based assays, immunologically based assays, biosensors, biochemical assays, spectrometric assays, wet chemistry assays, sequential injection analysis and flow injection analysis assays which are suitable for analyzing the presence of the compounds or parameters. Preferably, the analyzing means are designed to perform quantitative measurements. In one useful embodiment the analyzing means comprises solid support analytical means or devices which, e.g., may be in the form of test strips (also known as dry sticks) comprising appropriate reagent(s) that in the presence of the compound being analyzed generate(s) a detectable signal. Additionally, the analyzing means may comprise or may be operationally linked to means for storing and transporting such solid support analytical devices.

Additionally, the system of the present invention comprises means for detecting signals generated by the analytical means in the presence of a compound or parameter being analyzed. Such signals may e.g. be in the form of intensity, frequency, color, number etc. Any conventional means for detecting such analytical signals are encompassed by the present invention.

It is contemplated that the means for analyzing a plurality of compounds or parameters in a milk sample may be analytically linked, i.e., physically connected to a single means for collecting a milk sample as described above, but it is also conceivable that the analyzing means is analytically linked to a plurality of such milk sample collecting means, which, e.g., may be located at the milking site(s), i.e., the analyzing means and the milk collecting means may be spatially separated. When the analyzing means is linked to a plurality of sample collecting means, the thus collected milk samples are suitably transported to the analyzing means via a tube element, via a conveyer element or by hand. In any of these ways of transportation, the individual milk samples may be collected and transported in appropriate enclosure elements such as, e.g., bags of flexible polymeric material, containers of plastic, glass or metal or any other suitable sample container, In a further useful embodiment, the system according to the invention has means for analyzing a plurality of compounds or parameters placed at each milking site.

Furthermore, the system of the invention comprises means for processing the obtained signals to thereby convert these signals to a set of data which is indicative of the physiological and/or nutritional condition of the individual herd member. The means for signal processing are preferably in the form of a computer program which is executable on a computer system including an embedded software and designed to translate and to process the obtained signals and to carry out analysis of the obtained data in order to reveal physiological conditions such as mastitis, protein balance, ketosis and state in reproduction cycle.

Such analysis can be carried out in many ways, e.g. by comparing with previous data from the particular milking animal, and/or calculated mean values based on similar data from the specific herd, and/or from recent and/or previously obtained data from the specific milking animal.

In accordance with the invention the system comprises means for data storage of the obtained set of data which is descriptive of the physiological and/or nutritional condition of the individual herd member. For permanent storage of data, magnetic and optical media such as tapes, disks, flash, and CD-ROMs may be applied. Accordingly, the analytical measurement data for each milking animal are kept in the data storage allowing for analysis of periodical changes, and allowing data for specific milking animals to be compared as well as allowing for comparisons of data from different milking animals in order to provide a better identification of any abnormality or deviation from the baseline or the normal range. Furthermore, the system comprises data output means for delivering or presenting the obtained and processed data to the user, typically by print, visual and/or auditive means including telephones such as mobile telephones. Transmission of data to the user may be via the internet.

For the purpose of data analysis, the system according to the invention may comprise an internal database and/or an external database having multiple data relating to previous analysis of milk samples for the presence of compounds or parameters which are indicative of the physiological and/or nutritional condition of milk producing animal herd members. It will be appreciated, that in order to support these databases, software such as database management systems (DBMS) is required to handle the storage and retrieval of data, and in order to provide the user with commands to query and update the database. Examples of such database management systems include hierarchical and relational database management systems. The database management systems is preferably stored on a memory device and is executable for query on a computer system. Access to the management systems is conveniently via the internet.

In an advantageous embodiment the multiple data stored in the internal database and/or the external database are data selected from (i) the location of the milking site, (ii) data for time and frequency of sample collection, (iii) data identifying the individual herd members from which samples were collected, (iv) analytical data indicative of the physiological and/or nutritional condition of the herd member, and (v) historical data for the individual herd member. In one advantageous embodiment the external database comprises data descriptive of the physiological and/or nutritional condition collected from similar individual members of one or more corresponding milk producing animal herd(s).

Thus, it is contemplated that when a plurality of data obtained from individual herds are transmitted to and stored in the external database, this external or central database will, after a period of time, contain a substantial amount of organized data for many milking animals from many areas. Statistical processing of this large number of data is expected to allow for continuous improvements of early diagnosis of abnormal physiological and/or nutritional condition of milking animals such as cows. A significant advantage hereof is that such external and central databases will contain data from a large number of animals from a particular district or region, e.g., a whole country or even the whole world. The large number of data will provide a basis for extensive statistical processing of the data in order to reveal new information. As a special advantage any indications of the occurrence of epidemic illnesses among, e.g., cows is expected to be easier to reveal and recognize. It is contemplated that the communication to and from the external or central database may be via the internet.

It will be appreciated that the internal and external databases may comprise further data and information. Such additional data and information may be data representing diagnostic parameters, physiological parameters, physiological knowledge and data representing advises and recommendations relating to actions to be taken regarding specific results from the analysis.

In one aspect, the database management system is capable of comparing real time analytical data received from the signal detection means with data stored in the internal database and/or an external database and, based thereupon, transmitting an instruction message. Such an instruction message can e.g. be a message indicating that a specific herd member or group of herd members is ready for insemination, indicating that a specific herd member is in need for mastitis treatment or indicating that a specific herd member or group of herd members is in need for feeding scheme adjustment. The recipient of the instruction message may e.g. be a specified specialist such as a farmer, a veterinarian, an inseminator and a farm management consultant.

In a further embodiment the instruction message may be sent from the system, e.g. as a digital signal, to the milking system, such as an automatic milking system. Thus, it will be possible to divert milk of low quality, such as mastitic milk, from the ordinary high quality milk. Additionally, it is contemplated that the system according to the invention may comprise means, including "smart gates", adapted to receive an instruction message and as response hereto direct selected animals to selected sites so as to allow for the above mentioned treatments or actions.

In accordance with the above description, useful embodiments of the system of the invention comprise data storage means which comprises a database containing for each individual herd member multiple data related to previous analysis of milk samples from herd members for the presence of individual compounds or parameters including data for identifying the milking site, milk yield data, data to identify the individual herd members, data related to parity, reproduction state and lactation state of the herd members including data indicating points in time in the reproduction and lactation cycles, data for time of sample collections, historical analytical data for the physiological and nutritional state, historical data for compositions of milk samples, feeding scheme data, disease record data including data for previous disease treatments.

In yet another embodiment the data storage means of the present system is, or is operationally linked to, a data management system that is capable of comparing real time analytical data received from the signal detection means with data stored in the data storage means and, based thereupon, generating and transmitting an instruction message to the herd manager or any other recipient such as a veterinarian, an inseminator or a farm management consultant. Such an instruction message may e.g. indicate that a specific herd member or group of herd members is ready for insemination, that a specific herd member is in need of mastitis treatment and/or that at least one specific herd member or group of herd members is in need of a feeding scheme adjustment.

In a still further embodiment, the data storage means of the system is operably linked to a database comprising historical data descriptive of the physiological and nutritional condition collected from members of one or more different milk producing animal herds, said database either being part of the system or being an external database operationally linked to the system, e.g. via the internet.

In a further aspect, the invention pertains to a method for optimizing the production performance of a milk producing animal herd using the system as described above, the method comprising the steps of: (i) collecting at a milking site a milk sample from each individual member of the herd, (ii) contacting said sample with the analyzing means of the present system that, in the presence of at least one compound or parameter indicative of the physiological and/or nutritional condition of the herd member, generates a detectable signal/detectable signals, (iii) recording in the signal detection means the character of said signal(s) to provide a set of analytical data indicative of the presence and/or amount of said compound or parameter, (iv) having the generated data processed to provide a set of data descriptive of the physiological and/or nutritional condition of the individual herd member, and (v) taking, on the basis of the set of data provided, appropriate steps to improve or correct the physiological and/or nutritional condition of any of the herd members in need of such improvement or correction.

As mentioned above, the invention provides in a still further aspect a method for optimizing the production performance of a milk producing animal herd comprising a plurality of individual herd members using an automated or semi-automated system for optimizing the production performance of a milk producing animal herd, the system comprising the following interconnected means: (a) means for collecting a milk sample from an individual member of said herd, said means is connectable to the herd milking system, (b) means for recognizing a unique identification code assigned to each of the individual herd member, (c) means for storing data including data for the physiological and nutritional state of said each individual herd member including data indicating point in time in the reproduction and lactation cycles, (d) means for analyzing a plurality of compounds or parameters in a milk sample being collected, said plurality of compounds or parameters at least including a compound or parameter indicative of mastitis, a compound indicative of the reproduction cycle state, at least one compound indicative of the protein balance of the herd member and at least one compound indicative of the energy balance state of the herd member, said analyzing means comprising (i) separate means for analyzing individual compounds or parameters in the milk sample, each of said separate means is capable of generating a detectable signal in the presence of an individual milk compound or parameter, and (ii) means for detecting signals generated in the presence of a compound or parameter being analyzed, (e) means for converting the detected signals to a set of data that is indicative of the physiological and/or nutritional condition of said individual herd member, (f) means for storage of said set of data descriptive of the physiological and/or nutritional condition for said individual herd members, and (e) data output means.

This method comprises the steps of: (i) collecting at a milking site a milk sample from each individual member of the herd, (ii) contacting said sample with the analyzing means that, in the presence of at least one compound or parameter indicative of the physiological and/or nutritional condition of the herd member, generates a detectable signal/detectable signals, (iii) recording in the signal detection means the character of said signal(s) to provide a set of analytical data indicative of the presence and/or amount of said compound or parameter, (iv) having the generated data processed to provide a set of data descriptive of the physiological and/or nutritional condition of the individual herd member, and (v) taking, on the basis of the set of data provided, appropriate steps to improve or correct the physiological and/or nutritional condition of any of the herd members in need of such improvement or correction. In this method, all parameters, features and procedures are, otherwise as described above for the system of the invention.

As also described above, the present invention relates in another aspect to an apparatus for analyzing a plurality of compounds or parameters in a milk sample of an individual member of a milk producing animal herd.

The apparatus of the invention is useful in the system and the methods of the invention and it comprises: (i) separate means for analyzing individual compounds or parameters in the milk sample, each of said separate means is capable of generating a detectable signal in the presence of an individual sample compound or parameter, (ii) means for directing a part of the milk sample to each separate analyzing means, said directing means being controlled by means for storing data for the physiological and nutritional state of each individual herd member, including data indicating point in time in the reproduction and lactation cycles of said herd member, such that the directing means is only activated at pre-selected points in time or at pre-selected time intervals in the production or lactation cycles of the individual herd member, all of which features are as described above for the system and the methods of the invention.

In useful embodiments the apparatus further comprises means for detecting signals generated in the presence of a compound or parameter being analyzed and such an apparatus provided with means for connecting it with at least one of: (a) means for collecting a milk sample from an individual member of said herd, said means is connectable to the herd milking system, (b) means for recognizing an identification code of the individual herd member, (c) means for storing data including data for the physiological and nutritional state of said each individual herd member including data indicating point in time in the reproduction and lactation cycles, (d) means for converting the detected signals to a set of data that is indicative of the physiological and/or nutritional condition of said individual herd member, (e) means for storage of said set of data descriptive of the physiological and/or nutritional condition for said individual herd members, and (f) data output means, which are all as described hereinbefore.

The invention will be further illustrated by means of the following non-limiting examples and the drawings wherein.

EXAMPLE 1

Analyzing Equipment Means Arranged at a Milking Site

Figure 1:
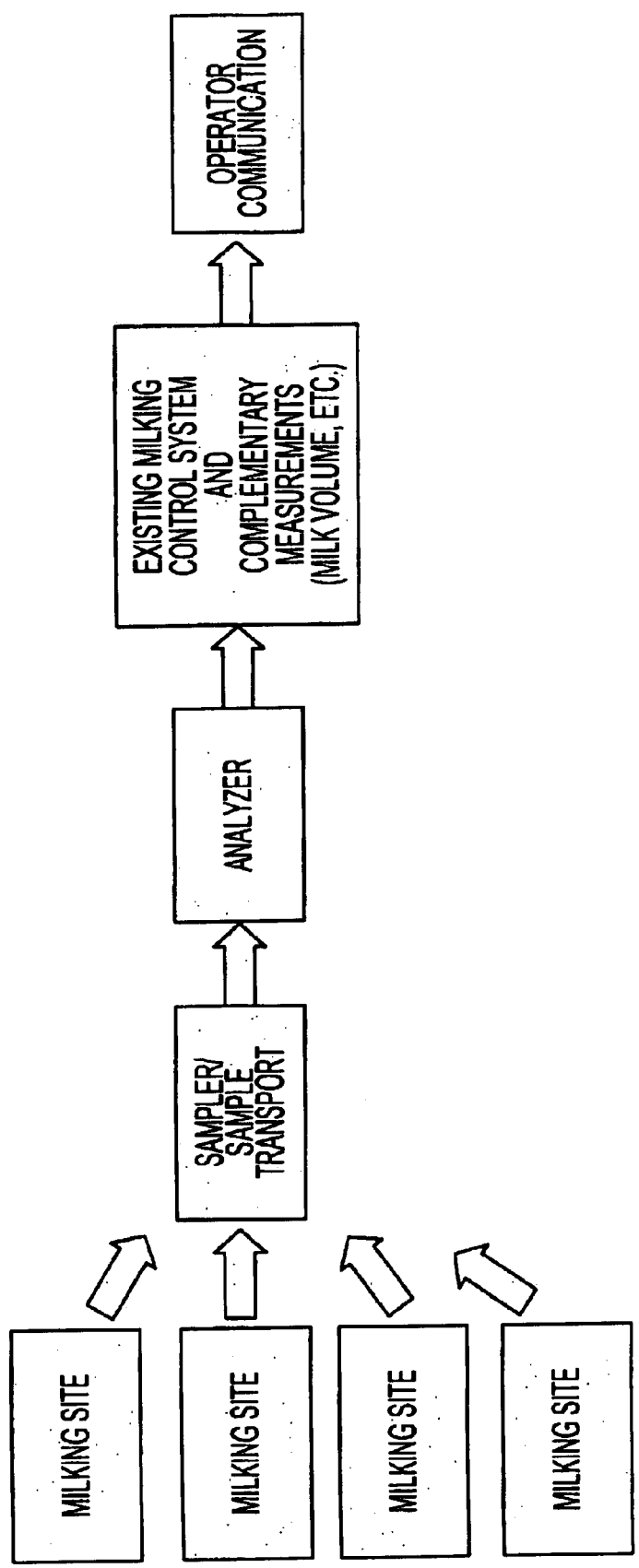
FIG. 1 shows an example of the system arranged at a milking site.

As an example, FIG. 1 shows the analyzing equipment for analyzing compounds indicative of the physiological condition of the milking animals arranged at a milking site in connection with sample collecting means. As can be seen from the figure, the sample collecting means is the physical connection between the milking points and the analyzing equipment. The function of the sample collecting means is to collect milk samples to be analyzed at an appropriate time during the milking process.

The milking site may be part of an automatic milking system for freely moving cows, carrying identification means, such as earmarks, or strips which may be electronically detected. In a further embodiment the milking site is one of several milking sites in a herringbone milking system. In the broadest aspect of this invention other kinds of milking sites may be applied, e.g., rotating or parallel parlors. As can also be seen from FIG. 1, the analyzing means may be combined with existing milking control system performing supplementary measurements such as milk volume, milk flow and temperature measurements.

At the milking site the identification of the cow is read and stored electronically. One or more samples are extracted from the milk flow. Sample(s) may extracted from at least one—preferably specifically identified—quarter (or mammary gland) of the udder. An advantageous alternative may be to extract samples from at least two quarters of one udder in order to compare the measurements on samples from the at least two quarters.

EXAMPLE 2

Data Handling System for Collecting, Storing and Processing Data

Figure 2:
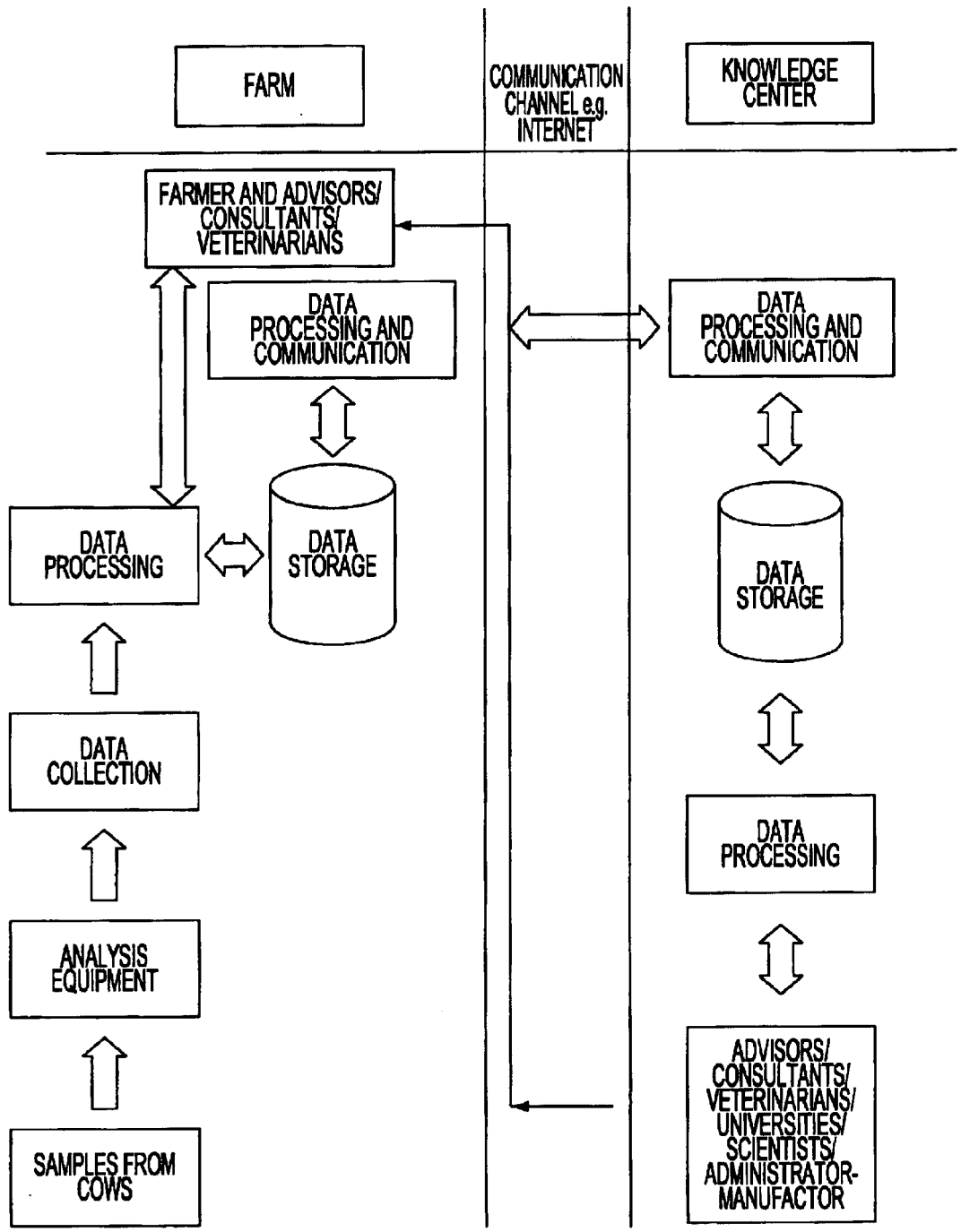
FIG. 2 shows an embodiment of a data handling system for collecting, storing and processing data.
Figure 3:
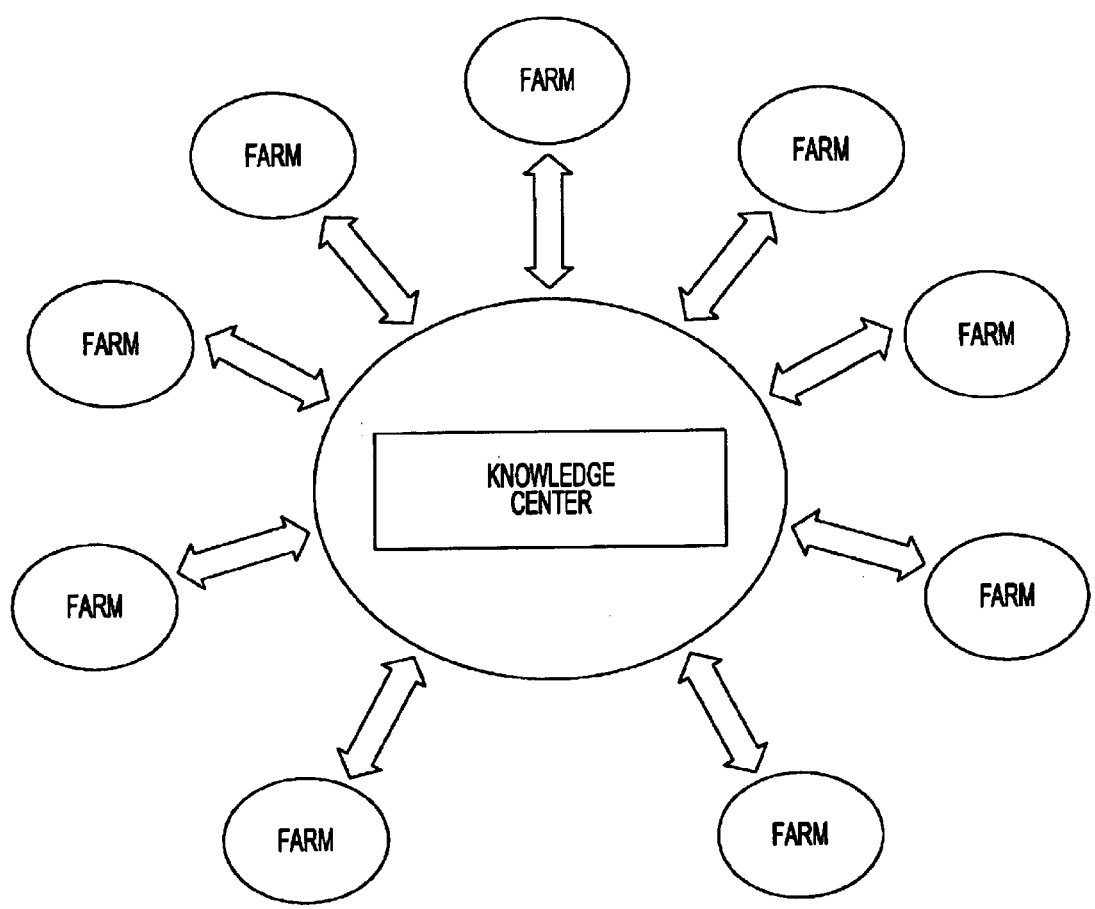
FIG. 3 shows a plurality of farmers coupled to a central system.

FIG. 2 illustrates one embodiment of the present invention. As can be seen from the example in FIG. 2, the system consists of a data system comprising a local arrangement at the farm including milk sample collecting means, analyzing means, data collection and processing, data storage, and further processing and transmission. As can be seen from FIG. 2, the processed data may be transmitted via a communication channel, such as the internet, to external databases. In the present example the transmitted data are received and stored in an external database at a knowledge centre, such as, e.g., DHIA (National Dairy Herd Improvement Association), a scientific centre or a university. The knowledge centre is accessible to a plurality of advisors, consultants, veterinarians, scientists etc. As can be seen from FIG. 2 the knowledge database is accessible to advisors, consultants etc. through the internet. As is further illustrated on FIG. 3, the data in the external database at the knowledge centre may be collected from a number of farms.

EXAMPLE 3

Chemical Analysis Equipment

As mentioned above, various appropriate chemical analysis equipment or analyzing means may be applied in order to perform the chemical analysis of the compounds indicative of the physiological condition of the milk producing animal.

Figure 4:
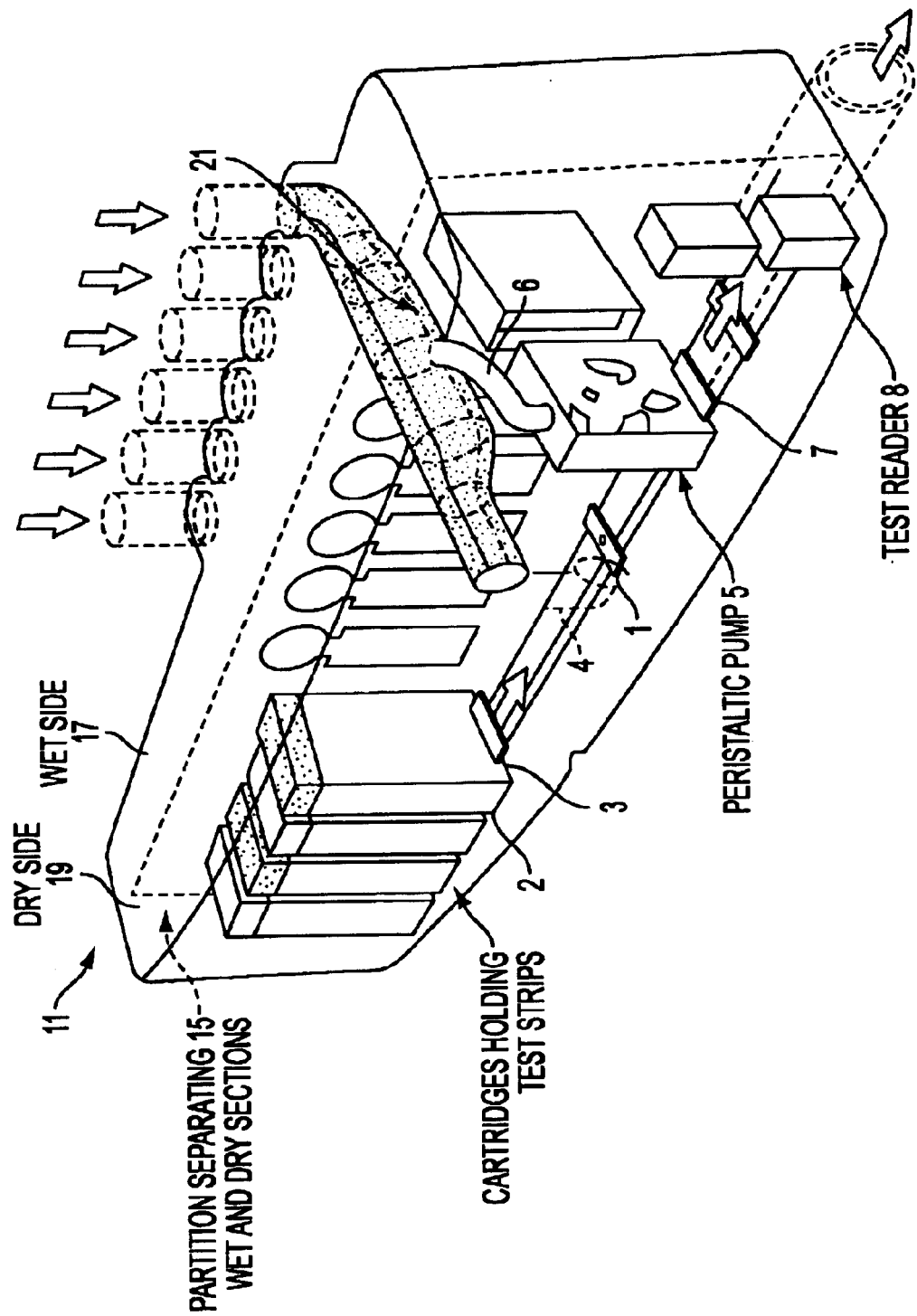
FIG. 4 shows one exemplary embodiment of analyzing means according to the invention.

FIG. 4 illustrates one example of such suitable chemical analysis equipment adapted to carry out the invention. Test strips or dry sticks 1 adapted to indicate the presence or amount of one or more of the desired compounds are stored in separate cartridges 2 holding the test strips. A test strip 3 is released from the cartridge to a conveyor belt 4. The conveyor belt advances the test strip towards a peristaltic pump 5. The inlet of peristaltic pump 6 is connected with the milk pipe line receiving milk from the milking equipment. As indicated in FIG. 4, the peristaltic pump 5 withdraws a small sample from the milk pipe line or the milk sample storage means, thereby transferring of few drops to the test strip 7. A chemical reaction takes place and the test strip is analyzed by a detector or test reader 8, such as a CCD camera or other photometry equipment, having a signal output port connected to a data collecting and processing device.

Figure 5:
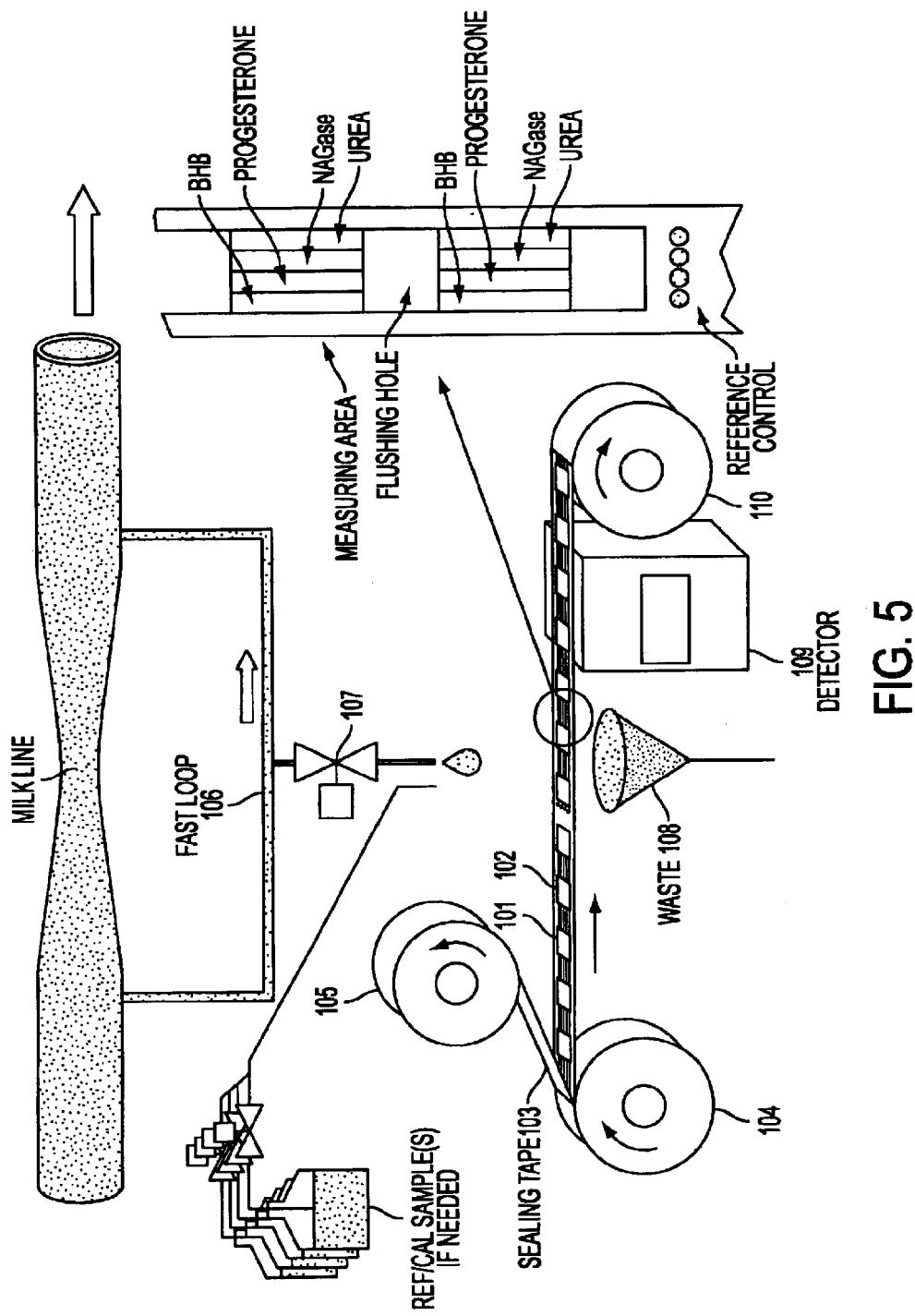
FIG. 5 shows a second exemplary embodiment of analyzing means according to the invention.

FIG. 5 illustrates another embodiment of analyzing means adapted to carry out the invention. Again, test stops or dry sticks 1 adapted to indicate the presence or amount of one or more of the desired compounds are arranged on a carrier tape 2 covered by a sealing tape 3. The tape is arranged on a spool 4. The sealing tape 3 is removed by rewinding on a second spool 5 shortly before the stick is exposed to the milk sample. A fast loop 6 extracts a fraction of the milk from the milk line. A valve 7 opens for a short time interval to release a few drops of milk onto a test strip 1. A funnel 8 located beneath the tape is arranged to receive the excess milk as waste. The tape is moved forward whereby the test strips 1 after having received a few drops of milk are exposed to the detector 9 and subsequently reminded on the spool 10. The detector can be a CCD camera or other photometry equipment having a signal output port connected to a data collecting and processing device. In a presently preferred embodiment the test strips or sticks on the tape are arranged to comprise at least 4 sensing areas: Acetone or BOHB (beta-hydroxyl-butyrate), progesterone, Nagase (beta-N-acetylhexosaminidase) or lactate dehydrogenase (LOH) and urea (milk urea nitrogen). It is however also contemplated to apply a tape having only one or two different sensing areas, such as sensing areas for the two most often applied compounds for indicating the physiological condition of the milk producing animal. Such compounds are, e.g., compounds indicating mastitis and milk urea nitrogen.

What is claimed is:

1. An automated or semi-automated system for optimizing the production performance of a milk producing animal herd comprising a plurality of individual herd members each assigned a unique identification code that is recognizable by the system, the system comprising the following interconnected means:
   (a) means for collecting a milk sample from an individual member of said herd, said means for collecting a milk sample being connectable to a herd milking system,
   (b) means for recognizing the identification code of the individual herd member,
   (c) means for storing data for a physiological condition, a nutritional condition or a combination of the physiological nutritional conditions of said each individual herd member,
   (d) means for analyzing a plurality of compounds or parameters in a milk sample being collected, said means for analyzing a plurality of compounds or parameters comprising:
      (i) separate means for analyzing individual compounds or parameters in the milk sample, each of said separate means for analyzing individual compounds or parameters being capable of generating a detectable signal in the presence of an individual milk compound or parameter,
      (ii) means for directing a part of the milk sample to each separate analyzing means, said directing means being controlled in response to at least one change for at least one parameter in at least one individual herd member recorded by said means for storing data for the physiological state condition, a nutritional condition or a combination of physiological and nutritional conditions of each individual herd member relative to previously-stored data in said means for storing data for said individual herd member such that the directing means is only activated at pre-selected points in time or at pre-selected time intervals in the reproduction or lactation cycles, or said directing means being controlled in response to a signal from said means for storing data such that the directing means is only activated at pre-selected points in time or at pre-selected time intervals in the reproduction or lactation cycles,
      (iii) means for detecting signals generated in the presence of a compound or parameter being analyzed,
   (e) means for converting the detected signals to a set of data that is indicative of the physiological condition, the nutritional condition or a combination of the physiological and nutritional conditions of said individual herd member,
   (f) means for storage of said set of data descriptive of the physiological condition, the nutritional condition or a combination of the physiological and nutritional conditions for said individual herd members, and
   (g) data output means for producing data output.

2. A system according to claim 1 where the sample collecting means is adapted to collect a milk sample from an individual mammary gland of a herd member.

3. A system according to claim 1 where the sample collecting means is adapted to collect a sample combining milk from two or more mammary glands of a herd member.

4. A system according to claim 2 or 3 where the sample collecting means is capable of collecting a proportional milk sample which is representative of average composition of total milk produced during the milking of each individual herd member.

5. A system according to claim 2 or 3 where the sample collecting means is capable of collecting a subsample during a pre-selected time interval of the milking operation.

6. A system according to claim 1 where the sample collecting means comprises means for storing a milk sample being collected.

7. A system according to claim 6 where the means for storing a milk sample comprises mixing means.

8. A system according to claim 6 where the sample collecting means further comprises or is operationally connected with at least one of: (i) means permitting the sample collecting means to be cleaned between samples, (ii) means for storing a buffer solution or a dilute solution, (iii) means for connecting the means for storing a milk sample to the means for analyzing a plurality of compounds or parameters, the means for storing a buffer solution or the dilute solution, the herd milking system, a sample discharge outlet or a combination of the milking system and the sample discharge outlet, (iv) means for controlling the temperature of the milk sample being collected or (v) means for transporting the milk sample being collected.

9. A system according to any of claims 1–3 or 6 where the sample collecting means comprises means for storing a plurality of milk samples.

10. A system according to claim 9 where the means for storing a plurality of milk samples is in the form of a device comprising a plurality of milk storage containers.

11. A system according to claim 10 where the device comprising a plurality of milk storage containers is insertable into the milk collecting means prior to collecting milk samples and is removable therefrom when the plurality of samples is collected for bringing it into operational contact with the analytical means.

12. A system according to claims 6 or 7 where the means for storing a milk sample has a pressure that is different from the pressure of the herd milking system to which said means is connected.

13. A system according to any of claims 1–3 or 6 where the means for collecting a milk sample is connected to an element of the herd milking system selected from the group consisting of a teat cup, a teat tube, a milk metering device and a milk transporting tube.

14. A system according to claim 13 where the means for collecting a milk sample is connected to a tubing element of the herd milking system.

15. A system according to claim 14 where the means for collecting a milk sample is provided with a separate milk metering device.

16. A system according to claim 1 where the separate means for analyzing individual compounds or parameters in the milk sample includes means for analyzing at least one compound or parameter selected from the group consisting of a compound or parameter that is indicative of mastitis, a compound or parameter that is indicative of the reproduction cycle state of the milking animal and a compound or parameter that is indicative of the energy and nutritional state of the milking animal.

17. A system according to claim 16 comprising separate analyzing means for analyzing a compound or parameter indicative of mastitis that is selected from the group consisting of somatic cells, microbial cells or parts thereof, an enzyme, a protein, a lipid, a mineral, a trace element, milk temperature, conductivity of the milk and a particle that is separable by filtration.

18. A system according to claim 17 where the compound indicative of mastitis is an enzyme, the amount of which is increased in milk from an inflamed mammary gland.

19. A system according to claim 18 where the enzyme is selected from the group consisting of lactate dehydrogenase (LDH) and beta-N-acetylglucosaminidase (NAGase) E.C. 3.2.1.52.

20. A system according to claim 19 where the separate analyzing means for analyzing NAGase is capable of detecting an amount or NAGase which is in the range of 0 to 0.1 U/ml and/or an amount of LDH which is in the range of 100 to 2000 U/ml, or a combination of an amount of NAGase, which is in the range of 0 to 0.1 U/ml and an amount of LDH which is in the range of 100 to 2000 U/ml.

21. A system according to claim 16 comprising separate analyzing means for analyzing a compound or parameter, the presence or amount of which in milk is indicative of the reproduction cycle state of the milking animal, that is selected from the group consisting of a compound that indicates pro-oestrus, a compound that is indicative of oestrus (heat), a compound that indicates di-oestrus and a compound that indicates pregnancy.

22. A system according to claim 21 where the compound indicative of the reproduction cycle state of the milking animal is a hormone.

23. A system according to claim where the hormone to be analyzed is progesterone.

24. A system according to claim 23 where the separate analyzing means for analyzing progesterone is capable of detecting an amount thereof in the milk sample which is in the range of 0 to 30 ng/ml.

25. A system according to claim 23 where the separate analyzing means for analyzing progesterone is capable of detecting an amount thereof in the milk sample which is in the range of 0 to 20 ng/ml.

26. A system according to claim 16 comprising separate analyzing means for analyzing a compound or parameter indicative of the energy and/or nutritional state of the milking animal that is selected from the group consisting of a compound or parameter that is indicative of the protein balance of the milking animal and a compound or parameter that is indicative of the overall energy balance of the milking animal.

27. A system according to claim 26 where the compound or parameter that is indicative of the protein balance of the milking animal is selected from the group consisting of milk urea nitrogen (MUN) and total milk protein.

28. A system according to claim 27 where the separate analyzing means for analyzing a compound or parameter that is indicative of the protein balance of the milking animal is capable of detecting an amount of MUN which is in the range of 0 to 1000 mg/l.

29. A system according to claim 27 where the separate analyzing means for analyzing a compound or parameter that is indicative of the protein balance of the milking animal is capable of detecting an amount of MUN which is in the range of 0 to 700 mg/l.

30. A system according to claim 26 where the compound or parameter that is indicative of the overall energy balance of the milking animal is selected from the group consisting of a ketone body compound and total milk fat content.

31. A system according to claim 30 where the ketone body compound is selected from the group consisting of acetolactate, beta-hydroxybutyrate (BOHB) and acetone.

32. A system according to claim 31 where the analyzing means for analyzing a compound or parameter that is indicative of the overall energy balance of the milking animal is capable of detecting an amount of BOHB which is in the range of 0 to 0.7 mM.

33. A system according to claim 1 where the separate means for analyzing an individual compound or parameter in the milk sample includes means for analyzing at least one compound selected from the group consisting of NAGase, progesterone, milk urea nitrogen, total protein content, BOHB, total fat content and milk yield.

34. A system according to any of claims 1–3, 6 or 16 where the means for analyzing a plurality of compounds or parameters in a milk sample is analytically linked to a plurality of means for collecting a milk sample.

35. A system according to claim 34 where milk samples collected by the plurality of means for collecting a milk sample are transported to the means for analyzing a plurality of compounds or parameters in a milk sample via a tube element, via a conveyer element or by hand.

36. A system according to claim 35 where each individual milk sample is collected in an enclosure element.

37. A system according to claim 34 where the means for analyzing a plurality of compounds or parameters in a milk sample is spatially separated from the plurality of means for collecting a milk sample.

38. A system according to any of claims 1–3, 6 or 16 where the means for analyzing a plurality of compounds or parameters is placed at each milking site.

39. A system according to claim 1 where the data storage means comprises a database containing for each individual herd member multiple data related to previous analysis of milk samples from herd members for the presence of individual compounds or parameters.

40. A system according to claim 39 where the multiple data include data selected from the group consisting of: data for identifying the milking site, milk yield data, data to identify the individual herd members, data related to parity, data related to reproduction state and lactation state of the herd members, data for time of sample collections, historical analytical data for the physiological and nutritional condition, historical data for compositions of milk samples, feeding scheme data, and disease record data.

41. A system according to claim 40, where the data related to reproduction state and lactation state of the herd members is data indicating points in time in the reproduction and lactation cycles.

42. A system according to claim 40, where the data related to disease record data includes data for previous disease treatments.

43. A system according to claim 39 the data storage means is, or is operationally linked to, a data management system that is capable of comparing real time analytical data received from the signal detection means with data stored in the data storage means and, based thereupon, generating and transmitting an instruction message to a herd manager.

44. A system according to claim 1 or 43 where the data storage means is operably linked to a database comprising historical data indicative of the physiological and nutritional condition collected from members of one or more different milk producing animal herds, said database either being part of the system for optimizing the production performance of a milk producing animal herd or being an external database operationally linked to the system for optimizing the production performance of a milk producing animal herd.

45. A system according to claim 44 where the external database is operationally linked to the system for optimizing the production performance of a milk producing animal herd via the internet.

46. A system according to claim 43 where the instruction message indicates that a specific herd member is ready for insemination.

47. A system according to claim 43 where the instruction message indicates that a specific herd member is in need of mastitis treatment.

48. A system according to claim 43 where the instruction message indicates that at least one specific herd member is in need of a feeding scheme adjustment.

49. A system according to claim 43 where the recipient of the instruction message is a pre-selected specialist.

50. A system according to claim 49, wherein the pre-selected specialist is a farmer, a veterinarian, an inseminator, or a farm management consultant.

51. A system according to claim 1 where the separate means for analyzing individual compounds or parameters comprises means for performing an analysis selected from the group consisting of an enzymatically based assay, an immunologically based assay, a biosensor analysis, a biochemical assay, a spectrometric assay and a flow injection based assay.

52. A system according to claim 51 where the separate means for analyzing individual compounds or parameters comprises solid support analytical devices.

53. A system according to claim 52 where the analyzing means comprises or is operationally linked to means for storing and transporting the solid support analytical devices.

54. A system according to claim 1 wherein the directing means is activated for at least one member of the animal herd in response to a detection of a change in at least one compound or parameter of the member of the animal herd, indicating an abnormality in the physiological or nutritional condition of the member of the animal herd.

55. A system according to claim 54 wherein the pre-selected points in time or pre-selected time intervals are scheduled subsequently to the detection.

56. A system according to claim 1, wherein said data for a physiological and nutritional condition of said individual herd member is data indicating point in time in the reproduction and lactation cycles.

57. A system according to any of claims 1–3 where the sample collecting means further comprises or is operationally connected with at least one of: (i) means permitting the sample collecting means to be cleaned between samples, (ii) means for storing a buffer solution or a dilute solution, (iii) means for storing a milk sample being collected, (iv) means for connecting the means for storing a milk sample to the means for analyzing a plurality of compounds or parameters, the means for storing a buffer solution or the dilute solution, the herd milking system, a sample discharge outlet or a combination of the milking system and the sample discharge outlet, (v) means for controlling the temperature of the milk sample being collected or (vi) means for transporting the milk sample being collected.

58. A method for optimizing the production performance of a milk producing animal herd using the system according to any of claims 1–3, 6, 16, 39 or 46, the method comprising the steps of:
(i) collecting at a milking site a milk sample from each individual member of the herd,
(ii) contacting said sample with the means for analyzing a plurality of compounds or parameters that, in the presence of at least one compound or parameter indicative of the physiological condition, the nutritional condition or a combination of the physiological and nutritional conditions of the herd member, generates at least one detectable signal,
(iii) recording in the signal detection means the character of said at least one signal to provide a set of analytical data indicative of the presence, the amount or a combination of the presence and the amount of said compound or parameter,
(iv) having the generated data processed to provide a set of data indicative of the physiological condition, the nutritional condition or a combination of the physiological and nutritional conditions of the individual herd member, and
(v) taking, on the basis of the set of data provided, appropriate steps to improve or correct the physiological condition, the nutritional condition or a combination of the physiological and nutritional conditions of any of the herd members in need of such improvement or correction.

59. A method for optimizing the production performance of a milk producing animal herd comprising a plurality of individual herd members using an automated or semi-automated system for optimizing the production performance of a milk producing animal herd, the system comprising the following interconnected means:
(a) means for collecting a milk sample from an individual member of said herd, said means is connectable to a herd milking system,
(b) means for recognizing a unique identification code assigned to each of the individual herd members,
(c) means for storing data including data for a physiological state condition, a nutritional condition, or a combination of physiological and nutritional conditions of said each individual herd member or data indicating point in time in the reproduction and lactation cycles,
(d) means for analyzing a plurality of compounds or parameters in a the milk sample being collected, said plurality of compounds or parameters including at least two of the following: a compound or parameter indicative of mastitis, a compound indicative of the reproduction cycle state, at least one compound indicative of the protein balance of the herd member or at least one compound indicative of the energy balance state of the herd member, said analyzing means comprising
  (i) separate means for analyzing individual compounds or parameters in the milk sample, each of said separate means for analyzing individual compounds or parameters is capable of generating at least one detectable signal in the presence of an individual milk compound or parameter, and
  (ii) means for detecting the at least one signal generated in the presence of a compound or parameter being analyzed,
(e) means for converting the at least one detected signal to a set of data that is indicative of the physiological condition, the nutritional condition or a combination of the physiological and nutritional conditions of said individual herd member,
(f) means for storage of said set of data indicative of the physiological condition, the nutritional condition or a combination of the physiological and nutritional conditions for said individual herd members, and
(g) a means for producing data output, the method comprising the steps of:
  (i) collecting at a milking site a milk sample from each individual member of the herd,
  (ii) contacting said sample with the means for analyzing a plurality of compounds or parameters that, in the presence of at least one compound or parameter indicative of the physiological condition, the nutritional condition or a combination of the physiological and nutritional conditions of the herd member, generates at least one detectable signal,
  (iii) recording in the signal detection means the character of said at least one detectable signal to provide a set of analytical data indicative of the presence, the amount, or a combination of the presence and the amount of said compound or parameter,
  (iv) having the generated data processed to provide a sat of data indicative of the physiological condition, the nutritional condition or a combination of the physiological and nutritional conditions of the individual herd member, and
  (v) taking, on the basis of the set of data provided, appropriate steps to improve or correct the physiological condition, the nutritional condition or a combination of the physiological and nutritional conditions of any of the herd members in need of such improvement or correction.

60. A method according to claim 59 using a system where the sample collecting means further comprises, or is operationally connected with, at least one of (i) means permitting the sample collecting means to be cleaned between samples, (ii) means for storing a buffer solution or a dilute solution, (iii) means for storing a milk sample being collected, (iv) means for connecting the means for storing a milk sample to the means for analyzing a plurality of compounds or parameters, the means for storing a buffer solution or the dilute solution, the herd milking system, a sample discharge outlet or a combination of the milking system and the sample discharge outlet, (v) means for controlling the temperature of the milk sample being collected and (vi) means for transporting the milk sample being collected.

61. A method according to claim 59 using a system where the sample collecting means is adapted to collect a milk sample from an individual mammary gland of a herd member.

62. A method according to claim 59 using a system where the sample collecting means is adapted to collect a sample combining milk from at least two mammary glands of a herd member.

63. A method according to claim 61 or 62 using a system where the sample collecting means is capable of collecting a proportional milk sample which is representative of average composition of total milk produced during the milking of each individual herd member.

64. A method according to claim 61 or 62 using a system where the sample collecting means is capable of collecting a subsample during a pre-selected time interval of the milking operation.

65. A method according to claim 59 using a system where the sample collecting means comprises means for storing a milk sample being collected.

66. A method according to claim 65 using a system where the means for storing a milk sample comprises mixing means for mixing the milk sample.

67. A method according to claim 65 using a system where the sample collecting means further comprises, or is operationally connected with, at least one of (i) means permitting the sample collecting means to be cleaned between samples, (ii) means for storing a buffer solution or a dilute solution, (iii) means for connecting the means for storing a milk sample to the means for analyzing a plurality of compounds or parameters, the means for storing a buffer solution or the dilute solution, the herd milking system, a sample discharge outlet or a combination of the herd milking system and a sample discharge outlet, (iv) means for controlling the temperature of the milk sample being collected and (v) means for transporting the milk sample being collected.

68. A method according to claim 59 or 65 using a system where the sample collecting means comprises means for storing a plurality of milk samples.

69. A method according to claim 68 using a system where the means for storing a plurality of milk samples is in the form of a device comprising a plurality of milk storage containers.

70. A method according to claim 69 using a system whore the device comprising a plurality of milk storage containers is inserted into the milk collecting means prior to collecting milk samples and is removed therefrom when the plurality of samples is collected for bringing it into operational contact with the means for analyzing a plurality of compounds or parameters.

71. A method according to claim 65 or 66 using a system where the means for storing a milk sample has a pressure that is different from the pressure of the herd milking system to which said means for storing a milk sample is connected.

72. A method according to claim 59 or 65 using a system where the means for collecting a milk sample is connected to an element of the herd milking system selected from the group consisting of a teat cup, a teat tube, a milk flow metering device, and a milk transporting tube.

73. A system according to claim 72 where the means for collecting a milk sample is connected to a tubing element of the herd milking system and is provided with a separate milk flow meter.

74. A method according to claim 59 where the compound indicative of mastitis is an enzyme, the amount of which is increased in milk from an inflamed mammary gland.

75. A method according to claim 74 where the enzyme is selected from the group consisting of lactate dehydrogenase (LDH) and beta-N-acetylglucosaminidase (NAGase) E.C. 3.2.1.52.

76. A method according to claim 75 using a system where the analyzing means for analyzing NAGase is capable of detecting an amount of NAGase which is in the range of 0 to 0.1 U/ml, an amount of LDH which is in the range of 100 to 2000 U/ml or a combination of NAGase in the range of 0 to 0.1 U/ml and LDH in the range of 100 to 2000 U/ml.

77. A method according to claim 59 using a system comprising said separate analyzing means for analyzing the individual compounds or parameters, which includes means for analyzing at least one compound or parameter the presence or amount of which in milk is indicative of the reproduction cycle state of the milking animal, that is selected from the group consisting of a compound that indicates pro-oestrus, a compound that is indicative of oestrus (heat), a compound that indicates di-oestrus and a compound that indicates pregnancy.

78. A method according to claim 77 where the compound indicative of the reproduction cycle state of the milking animal is a hormone.

79. A method according to claim 78 where the hormone to be analyzed is progesterone.

80. A method according to claim 79 using a system comprising analyzing means for analyzing progesterone that is capable of detecting an amount thereof in the milk sample which is in the range of 0 to 30 ng/ml.

81. A method according to claim 59 using a system where the compound or parameter that is indicative of the protein balance of the milking animal is selected from the group consisting of milk urea nitrogen (MUN) and total milk protein.

82. A method according to claim 81 using a system where the analyzing means for analyzing a compound or parameter that is indicative of the protein balance of the milking animal is capable of detecting an amount of MUN which is in the range of 0 to 1000 mg/l.

83. A method according to claim 81 using a system where the analyzing means for analyzing a compound or parameter that is indicative of the protein balance of the milking animal is capable of detecting an amount of MUN which is in the range of 0 to 700 mg/l.

84. A method according to claim 59 where the compound or parameter that is indicative of the energy balance of the milking animal is selected from the group consisting of a ketone body compound and total milk fat content.

85. A method according to claim 84 where the ketone body compound is selected from the group consisting of acetolactate, beta-hydroxybutyrate (BOHB) and acetone.

86. A method according to claim 85 using a system where the analyzing means for analyzing a compound or parameter that is indicative of the energy balance of the milking animal is capable of detecting an amount of BOHB which is in the range of 0 to 0.7 mM.

87. A method according to claim 85 using a system where the analyzing means for analyzing a compound or parameter that is indicative of the energy balance of the milking animal is capable of detecting an amount of BOHB which is in the range of 0.1 to 0.7 mM.

88. A method according to any of claims 59, 65 or 74 using a system where the means for analyzing a plurality of compounds or parameters in a milk sample is analytically linked to a plurality of means for collecting a milk sample.

89. A method according to claim 88 where the milk sample collected by the means for collecting a milk sample is transported to the means for analyzing a plurality of compounds or parameters in a milk sample via a tube element, via a conveyer element or by hand.

90. A method according to claim 88 where each individual milk sample is collected in an enclosure element.

91. A method according to claim 88 where the means for analyzing a plurality of compounds or parameters in a milk sample is spatially separated from the plurality of means for collecting a milk sample.

92. A method according to claim 59 using a system where the data storage means comprises a database including for each individual herd member multiple data related to previous analysis of milk samples from herd members for the presence of individual compounds or parameters.

93. A method according to claim 92 where the multiple data include data selected from the group consisting of data for identifying the milking site, milk yield data, data to identify the individual herd members, data related to parity, reproduction state and lactation state of the herd members, data for time of sample collections, historical analytical data for the physiological and nutritional condition, historical data for compositions of milk samples, feeding scheme data, and disease record data.

94. A method according to claim 93 where the reproduction state and lactation state of the herd members includes data indicating points in time in the reproduction and lactation cycles.

95. A method according to of claim 93 where the disease record data includes data for previous disease treatments.

96. A method according to claim 92 where the data storage means is, or is operationally linked to, a data management system that is capable of comparing real time analytical data received from the signal detection means with data stored in the data storage means and, based thereupon, generating and transmitting an instruction message to a herd manager.

97. A method according to claim 59 or 96 using a system where the data storage means is operationally linked to a database comprising historical data indicative of the physiological and nutritional condition collected from members of one or more different milk producing animal herds, said database either being part of the system or being an external database operationally linked to the system.

98. A method according to claim 97 where the external database is operationally linked to the system via the internet.

99. A method according to claim 96 where the instruction message indicates that a specific herd member is ready for insemination or becomes pregnant.

100. A method according to claim 96 where the instruction message indicates that a specific herd member is in need of mastitis treatment.

101. A method according to claim 96 where the instruction message indicates that at least one herd member is in need of a feeding scheme adjustment.

102. A method according to claim 96 where the recipient of the instruction message is a pro-selected specialist.

103. A method according to claim 102, wherein the pre-selected specialist is a farmer, a veterinarian, or a farm management consultant.

104. A method according to claim 59 using a system where the separate means for analyzing individual compounds or parameters comprises means for performing an analysis selected from the group consisting of an enzymatically based assay, an immunologically based assay, a biosensor analysis, a biochemical assay, a spectrometric assay and a flow injection based assay.

105. A method according to claim 104 where the separate means for analyzing individual compounds or parameters comprises solid support analytical devices.

106. A method according to claim 105 where the separate means for analyzing individual compounds or parameters comprises or is operably linked to a means for storing and transporting the solid support analytical devices.

107. An apparatus for analyzing a plurality of compounds or parameters in a milk sample of an individual member of a milk producing animal herd, said apparatus comprising:
  (i) separate means for analyzing individual compounds or parameters in the milk sample, each of said separate means being capable of generating a detectable signal in the presence of an individual sample compound or parameter,
  (ii) means for directing a part of the milk sample to each separate analyzing means, said directing means being controlled in response to at least one change for at least one parameter in at least one individual herd member recorded by said means for storing data for a physiological condition, a nutritional condition or a combination of the physiological and nutritional conditions of each individual herd member relative to the data in said means for storing data for said individual herd member, such that the directing means is only activated at pro-selected points in time or at pre-selected time intervals in the reproduction or lactation cycles, of the individual herd member or said directing means being controlled in response to a signal from said means for storing data such that the directing means is only activated at pre-selected points in time or at pre-selected time intervals in the reproduction or lactation cycles of the individual herd member.

108. An apparatus according to claim 107 further comprising means for detecting signals generated in the presence of a compound or parameter being analyzed.

109. An apparatus according to claim 107 or 108 provided with means for connecting the apparatus with at least one of:
  (a) means for collecting a milk sample from an individual member of said herd, said means is connectable to a herd milking system,
  (b) means for recognizing an identification code of the individual herd member,
  (c) means for storing data,
  (d) means for converting the detected signals to a set of data that is indicative of the physiological condition, the nutritional condition or a combination of the physiological and nutritional conditions of said individual herd member,
  (e) means for storage of said set of data indicative of the physiological condition, the nutritional condition or a combination of the physiological and nutritional conditions for said individual herd members, and
  (f) data output means for producing data output.

110. An apparatus according to claim 109, wherein said means for storing data is a means for storing data on the physiological and nutritional condition state of said each individual herd member.

111. An apparatus according to claim 109, wherein said means for storing data is a means for indicating point in time in the reproduction and lactation cycles.

112. An apparatus according to claim 107, where the directing means is controlled by a data indicating point in time on the reproduction and lactation cycles of said herd member.

113. An apparatus according to claim 107 wherein the directing means is activated for at least one member of the animal herd in response to a detection of a change in at least one compound or parameter of the member of the animal herd, indicating an abnormality in the physiological or nutritional condition of the member of the animal herd.

114. An apparatus according to claim wherein the pre-selected points in time or pre-selected time intervals are scheduled subsequently to the detection.

115. A method for optimizing the production performance of a milk producing animal herd comprising a plurality of individual herd members using an automated or semi-automated system for optimizing the production performance of a milk producing animal herd, the system comprising the following interconnected means:
  (a) means for collecting a milk sample from an individual member of said herd, said means is connectable to a herd milking system,
  (b) means for recognizing a unique identification code assigned to each of the individual herd members,
  (c) means for storing data including data for a physiological condition, a nutritional condition or a combination of physiological and nutritional conditions of said each individual herd member or data indicating point in time in the reproduction and lactation cycles,
  (d) means for analyzing a plurality of compounds or parameters in a milk sample being collected, said plurality of compounds or parameters including at least one of a compound or parameter indicative of mastitis, a compound indicative of the reproduction cycle state, at least one compound indicative of the protein balance of the herd member or at least one compound indicative of the energy balance state of the herd member, said analyzing means comprising
    (i) separate means for analyzing individual compounds or parameters in the milk sample, each of said separate means for analyzing individual compounds or parameters is capable of generating at least one detectable signal in the presence of an individual milk compound or parameter, and
    (ii) means for detecting the at least one signal generated in the presence of a compound or parameter being analyzed,
  (e) means for converting the at least one detected signal to a set of data that is indicative of the physiological condition, the nutritional condition or a combination of the physiological and nutritional conditions of said individual herd member,
  (f) means for storage of said set of data indicative of the physiological condition, the nutritional condition or a combination of the physiological and nutritional conditions for said individual herd members, and
  (g) a means for producing data output, the method comprising the steps of:
    (i) collecting at a milking site a milk sample from each individual member of the herd,
    (ii) contacting said sample with the means for analyzing a plurality of compounds or parameters that, in the presence of at least one compound or parameter indicative of the physiological condition, the nutritional condition or a combination of the physiological and nutritional conditions of the herd member, generates at least one detectable signal,
    (iii) recording in the signal detection means the character of said at least one detectable signal to provide a set of analytical data indicative of the presence, the amount, or a combination of the presence and the amount of said compound or parameter,
    (iv) having the generated data processed to provide a set of data indicative of the physiological condition, the nutritional condition or a combination of the physiological and nutritional conditions of the individual herd member, and
    (v) taking, on the basis of the set of data provided, appropriate steps to improve or correct the physiological condition, the nutritional condition or a combination of the physiological and nutritional conditions of any of the herd members in need of such improvement or correction.

116. A method for optimizing the production performance of a milk producing animal herd comprising a plurality of individual herd members using an automated or semi-automated system for optimizing the production performance of a milk producing animal herd, the system comprising the following interconnected means:
  (a) means for collecting a milk sample from an individual member of said herd, said means is connectable to a herd milking system,
  (b) means for recognizing a unique identification code assigned to each of the individual herd members,
  (c) means for storing data including data for a physiological state condition, a nutritional condition or a combination of physiological and nutritional conditions of said each individual herd member or data indicating point in time in the reproduction and lactation cycles,
  (d) means for analyzing a plurality of compounds or parameters in a milk sample being collected, said plurality of compounds or parameters including at least one of a compound or parameter indicative of mastitis, a compound indicative of the reproduction cycle state, at least one compound indicative of the protein balance of the herd member or at least one compound indicative of the energy balance state of the herd member, said analyzing means comprising
    (i) separate means for analyzing individual compounds or parameters in the milk sample, each of said separate means for analyzing individual compounds or parameters is capable of generating at least one detectable signal in the presence of an individual milk compound or parameter, and
    (ii) means for detecting the at least one signal generated in the presence of a compound or parameter being analyzed,
  (e) means for converting the at least one detected signal to a set of data that is indicative of the physiological condition, the nutritional condition or a combination of the physiological and nutritional conditions of said individual herd member,
  (f) means for storage of said set of data indicative of the physiological condition, the nutritional condition or a combination of the physiological and nutritional conditions for said individual herd members, and
  (g) a means for producing data output, the method comprising the steps of:
    (i) collecting at a milking site a milk sample from each individual member of the herd,
    (ii) contacting said sample with the means for analyzing a plurality of compounds or parameters that, in the presence of at least one compound or parameter indicative of the physiological condition, the nutritional condition or a combination of the physiological and nutritional conditions of the herd member, generates at least one detectable signal,
    (iii) recording in the signal detection means the character of said at least one detectable signal to provide a set of analytical data indicative of the presence, the amount, or a combination of the presence and the amount of said compound or parameter, said character indicating a change in the presence, the amount or a combination of the presence and the amount of said compound or parameter for at least one member of the herd, relative to the date in said means for storing data, for said herd member,
    (iv) having the generated data processed to provide a set of data indicative of the physiological condition, the nutritional condition or a combination of the physiological and nutritional conditions of the individual herd member,
    (v) changing the frequency or the timing of the contacting of a part of a milk sample with the analyzing means until the physiological condition, the nutritional condition or a combination of the physiological and nutritional conditions of said herd member is improved or corrected, and
    (vi) taking, on the basis of the set of data provided, appropriate steps to improve or correct the physiological condition, the nutritional condition or a combination of the physiological and nutritional conditions of any of the herd members in need of such improvement or correction.

117. A method for optimizing the production performance of a milk producing animal herd comprising a plurality of individual herd members using an automated or semi-automated system for optimizing the production performance of a milk producing animal herd, the system comprising the following interconnected means:
  (a) means for collecting a milk sample from an individual member of said herd, said means is connectable to a herd milking system,
  (b) means for recognizing a unique identification code assigned to each of the individual herd members,
  (c) means for storing data including data for a physiological state condition, a nutritional condition or a combination of physiological and nutritional conditions of said each individual herd member or data indicating point in time in the reproduction and lactation cycles,
  (d) means for analyzing a plurality of compounds or parameters in a milk sample being collected, said plurality of compounds or parameters including at least two of the following: a compound or parameter indicative of mastitis, a compound indicative of the reproduction cycle state, at least one compound indicative of the protein balance of the herd member or at least one compound indicative of the energy balance state of the herd member, said analyzing means comprising
    (i) separate means for analyzing individual compounds or parameters in the milk sample, each of said separate means for analyzing individual compounds or parameters is capable of generating at least one detectable signal in the presence of an individual milk compound or parameter, and
    (ii) means for detecting the at least one signal generated in the presence of a compound or parameter being analyzed,
  (e) means for converting the at least one detected signal to a set of data that is indicative of the physiological condition, the nutritional condition or a combination of the physiological and nutritional conditions of said individual herd member,
  (f) means for storage of said set of data indicative of the physiological condition, the nutritional condition or a combination of the physiological and nutritional conditions for said individual herd members, and
  (g) a means for producing data output, the method comprising the steps of:
    (i) collecting at a milking site a milk sample from each individual member of the herd, (ii) contacting said sample with the means for analyzing a plurality of compounds or parameters that, in the presence of at least one compound or parameter indicative of the physiological condition, the nutritional condition or a combination of the physiological and nutritional conditions of the herd member, generates at least one detectable signal, (iii) recording in the signal detection moans the character of said at least one detectable signal to provide a set of analytical data indicative of the presence, the amount or a combination of the presence and the amount of said compound or parameter said character indicting a change the presence, the amount or a combination of the presence and the amount of said compound or parameter for at least one member of the herd, relative to the data in said means for storing data, for said herd member, (iv) having the generated data processed to provide a set of data indicative of the physiological condition, the nutritional condition or a combination of the physiological and nutritional conditions of the individual herd member, (v) changing the frequency or the timing of the contacting of a part of a milk sample with the analyzing means until the physiological condition, the nutritional condition or a combination of the physiological and nutritional conditions of said herd member is improvement or corrected, and (vi) taking, on the basis of the set of data provided, appropriate steps to improve or correct the physiological condition, the nutritional condition or a combination of such improvement or correction.

* * * * *

UNITED STATES PATENT AND TRADEMARK OFFICE
CERTIFICATE OF CORRECTION

| | |
|---|---|
| PATENT NO. | : 6,814,025 B2 |
| APPLICATION NO. | : 10/091782 |
| DATED | : November 9, 2004 |
| INVENTOR(S) | : Fei Chen et al. |

It is certified that error appears in the above-identified patent and that said Letters Patent is hereby corrected as shown below:

Title Page, item [54]
The Title "SYSTEM FOR OPTIMISING THE PRODUCTION OF A MILK PRODUCING ANIMAL HERD" should be changed to --SYSTEM FOR OPTIMISING THE PRODUCTION PERFORMANCE OF A MILK PRODUCING ANIMAL HERD--

Column 6, line 50, delete "tar" and insert --for--.
Column 8, line 11, delete "tar" and insert --for--.
Column 11, line 10, delete "vanes" and insert --varies--.
Column 12, line 2, delete "acetone, in" and insert --acetone. In--; line 57, delete "far" and insert --for--; line 59, delete "pro" and insert --pre--; and line 62, delete "far" and insert --for--.
Column 19, line 11, delete "stops" and insert --strips--; line 28, "4" should not be bolded; and line 30, delete "LOH" and insert --LDH--.

Claim 1, column 19, line 52, before "nutritional" insert --and--; and column 20, line 2, delete "state".
Claim 20, column 21, line 44, delete "or" and insert --of--.
Claim 23, column 21, line 60, after "claim" insert --22--.
Claim 59, column 24, line 61, delete "state"; and line 66, delete "a".
Claim 70, column 26; line 39, delete "whore" and insert --where--.
Claim 116, column 31, line 17, delete "state".
Claim 117, column 32, line 32, delete "state";
column 33, line 8, delete "moans" and insert --means--;
column 33, line 13, delete "indicting" and insert --indicating-- and after "change" insert --in--;

UNITED STATES PATENT AND TRADEMARK OFFICE
CERTIFICATE OF CORRECTION

PATENT NO. : 6,814,025 B2
APPLICATION NO. : 10/091782
DATED : November 9, 2004
INVENTOR(S) : Fei Chen et al.

It is certified that error appears in the above-identified patent and that said Letters Patent is hereby corrected as shown below:

column 34, line 11, delete "improvement" and insert --improved--; and
column 34, line 15, after "of" insert --the physiological and nutritional conditions of any of the herd members in need of--.

Signed and Sealed this

First Day of April, 2008

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 6,814,025 B2 |
| APPLICATION NO. | : 10/091782 |
| DATED | : November 9, 2004 |
| INVENTOR(S) | : Fei Chen et al. |

It is certified that error appears in the above-identified patent and that said Letters Patent is hereby corrected as shown below:

Title Page, item [54] and Column 1, lines 1-3
The Title "SYSTEM FOR OPTIMISING THE PRODUCTION OF A MILK PRODUCING ANIMAL HERD" should be changed to --SYSTEM FOR OPTIMISING THE PRODUCTION PERFORMANCE OF A MILK PRODUCING ANIMAL HERD--

Column 6, line 50, delete "tar" and insert --for--.
Column 8, line 11, delete "tar" and insert --for--.
Column 11, line 10, delete "vanes" and insert --varies--.
Column 12, line 2, delete "acetone, in" and insert --acetone. In--; line 57, delete "far" and insert --for--; line 59, delete "pro" and insert --pre--; and line 62, delete "far" and insert --for--.
Column 19, line 11, delete "stops" and insert --strips--; line 28, "4" should not be bolded; and line 30, delete "LOH" and insert --LDH--.

Claim 1, column 19, line 52, before "nutritional" insert --and--; and column 20, line 2, delete "state".
Claim 20, column 21, line 44, delete "or" and insert --of--.
Claim 23, column 21, line 60, after "claim" insert --22--.
Claim 59, column 24, line 61, delete "state"; and line 66, delete "a".
Claim 70, column 26; line 39, delete "whore" and insert --where--.
Claim 116, column 31, line 17, delete "state".
Claim 117, column 32, line 32, delete "state";
column 33, line 8, delete "moans" and insert --means--;
column 33, line 13, delete "indicting" and insert --indicating-- and after "change" insert --in--;

UNITED STATES PATENT AND TRADEMARK OFFICE
CERTIFICATE OF CORRECTION

PATENT NO. : 6,814,025 B2
APPLICATION NO. : 10/091782
DATED : November 9, 2004
INVENTOR(S) : Fei Chen et al.

It is certified that error appears in the above-identified patent and that said Letters Patent is hereby corrected as shown below:

column 34, line 11, delete "improvement" and insert --improved--; and
column 34, line 15, after "of" insert --the physiological and nutritional conditions of any of the herd members in need of--.

This certificate supersedes the Certificate of Correction issued April 1, 2008.

Signed and Sealed this

Sixth Day of May, 2008

JON W. DUDAS
*Director of the United States Patent and Trademark Office*